US012654163B2

(12) United States Patent
Turzi et al.

(10) Patent No.: US 12,654,163 B2
(45) **Date of Patent: *Jun. 16, 2026**

(54) VIRAL INFECTIONS—TREATMENT WITH CONVALESCENT PLASMA/SERUM

(71) Applicant: REGEN LAB SA, Le Mont-sur-Lausanne (CH)

(72) Inventors: Antoine Turzi, Lauenen b. Gstaad (CH); Andreas Pigni, Geneva (CH); Farid Gomri, Prilly (CH); Hosni Trabelsi, Thonon les bains (FR)

(73) Assignee: Regen Lab USA LLC, Brooklyn, NY (US)

( * ) Notice: Subject to any disclaimer, the term of this patent is extended or adjusted under 35 U.S.C. 154(b) by 904 days.

This patent is subject to a terminal disclaimer.

(21) Appl. No.: 17/916,507

(22) PCT Filed: Mar. 30, 2021

(86) PCT No.: PCT/EP2021/058383

§ 371 (c)(1),
(2) Date: Sep. 30, 2022

(87) PCT Pub. No.: WO2021/198312

PCT Pub. Date: Oct. 7, 2021

(65) Prior Publication Data

US 2023/0133549 A1 May 4, 2023

(30) Foreign Application Priority Data

Mar. 30, 2020 (GB) ..................................... 2004649

(51) Int. Cl.
*B01L 3/00* (2006.01)
*A61K 35/16* (2015.01)
(Continued)

(52) U.S. Cl.
CPC .......... *B01L 3/50215* (2013.01); *A61K 35/16* (2013.01); *A61K 35/28* (2013.01);
(Continued)

(58) Field of Classification Search
CPC ........................... A61M 1/029; B01L 3/50215
(Continued)

(56) References Cited

U.S. PATENT DOCUMENTS

| | | | | |
|---|---|---|---|---|
| 4,190,535 A * | 2/1980 | Luderer | ............... | G01N 33/491 210/789 |
| 2018/0110917 A1* | 4/2018 | Turzi | ...................... | A61P 17/00 |

FOREIGN PATENT DOCUMENTS

| | | |
|---|---|---|
| CN | 1449833 A | 10/2003 |
| EP | 0733357 B1 | 7/2002 |

(Continued)

OTHER PUBLICATIONS

Turzi, A., et al., PCT/EP2021/058383, International Search Report, Jun. 25, 2021, 4 pages.

(Continued)

*Primary Examiner* — Walter E Webb
(74) *Attorney, Agent, or Firm* — Rahman LLC

(57) ABSTRACT

A container for use in the treatment and/or prophylaxis of viral infections and/or associated conditions prefilled with a thixotropic gel characterized by a density selected from about 1.02 g/cm$^3$ to about 1.05 g/cm$^3$.

8 Claims, 2 Drawing Sheets

(51) Int. Cl.

| | |
|---|---|
| ***A61K 35/28*** | (2015.01) |
| ***A61L 2/10*** | (2026.01) |
| ***A61L 2/26*** | (2006.01) |
| ***A61L 103/00*** | (2026.01) |
| ***A61P 31/14*** | (2006.01) |

(52) U.S. Cl.
CPC .................................... *A61L 2/10* (2013.01); *A61L 2/26* (2013.01); *A61P 31/14* (2018.01); *A61L 2103/23* (2026.01); *A61L 2202/11* (2013.01); *A61L 2202/16* (2013.01); *B01L 2200/16* (2013.01); *B01L 2300/069* (2013.01); *B01L 2300/0832* (2013.01)

(58) Field of Classification Search
USPC .......................................................... 424/484
See application file for complete search history.

(56) References Cited

FOREIGN PATENT DOCUMENTS

| | | | |
|---|---|---|---|
| EP | 3111974 | B1 | 8/2020 |
| WO | 2019155391 | A1 | 8/2019 |

OTHER PUBLICATIONS

Turzi, A., et al., PCT/EP2021/058383, Written Opinion, Jun. 25, 2021, 9 pages.

* cited by examiner

VIRAL INFECTIONS—TREATMENT WITH CONVALESCENT PLASMA/SERUM

TECHNICAL FIELD

The medical devices, compositions and methods described herein relates to treating coronavirus infections, viral hemorrhagic fever and associated conditions with convalescent plasma and/or convalescent serum preparations.

BACKGROUND

Coronaviruses can cause disease in animals such as humans. SARS (Severe Acute Respiratory Syndrome) and Middle East Respiratory Syndrome Coronavirus (MERS-CoV) are examples of such a disease. Recently, a new coronavirus has emerged, the severe acute respiratory syndrome coronavirus 2 (SARS-CoV-2), previously known as 2019-nCoV or "novel coronavirus 2019", with related condition COVID-19 associated with human fatalities. COVID-19 has been identified as a pandemic by the World Health Organization (the WHO) and has been reported in nearly all countries worldwide. It is a highly pathogenic respiratory virus that causes severe respiratory distress. Coronaviruses attach to the membrane of cells via interaction of their Spike (S) glycoproteins on the surface of the virion with their cognate receptor on host cells (e.g. dipeptidyl peptidase 4 (DPP4), found on a variety of human cells including lung and kidney cells). The S glycoprotein consists of an N-terminal S I domain that contains the receptor binding domain (RBD) and an S2 domain responsible for vims-cell fusion. Generally, in coronaviruses, including SARS-CoV, antibodies to the RBD are able to neutralize and inhibit growth of the virus in vitro. In mouse models of SARS-CoV, vaccine induced and passively transferred neutralizing antibodies have proven to be effective in inhibiting lung pathogenesis and death. However, Antibody Dependent Enhancement (ADE) in human immune cells has been reported for SARS CoV in vitro though its clinical significance in vivo is unknown.

Viral hemorrhagic fever is a clinical syndrome associated with significant mortality and morbidity. Hemorrhagic fever viruses generally belong to four viral families: the Filoviridae (e.g., Ebola virus, Marburg virus), Arenaviridae (e.g., Lassa virus, Junin virus), Bunyaviridae (e.g., Rift Valley fever virus, Crimean-Congo hemorrhagic fever virus), and Flaviviridae (e.g., dengue fever virus, Omsk hemorrhagic fever virus). These hemorrhagic fever viruses produce a wide range of disease severity and morbidities, with the most extreme conditions including circulatory instability, increased vascular permeability, and diffuse hemorrhage. Liver injury and hepatic dysfunction is another common occurrence in viral hemorrhagic fever. The underlying disease mechanisms associated with viral hemorrhagic fevers is complex, and may include among others, thrombocytopenia, disseminated intravascular coagulation (DIC), endothelial cell damage and dysfunction, activation of coagulation pathways, fibrin deposition and decreased levels of coagulation factors in blood.

Currently, no effective treatment has been identified for patients suffering from coronavirus infections or hemorrhagic fever virus. Interferon and ribavirin show limited effect against these agents. Evaluation of antibody therapies, including monoclonal and polyclonal antibody preparations, as well as passive transfer of blood or blood components from convalescent donors, has produced variable results in humans and animal models, with none approved for use in humans. In the case of passive transfer of blood products from convalescent donors, an additional risk of transfusion transmitted infection due to other pathogens presents further concerns. Human convalescent plasma with immunoglobulin has been used to some extent to prevent and treat viral infectious agents (Convalescent plasma as a potential therapy for COVID-19, The Lancet, Vol 20, April 2020, pp 398-400, Long Chen, Jing Xiong, Lei Bao, Yuan Shi).

In the absence of specific pharmaceutical or biologic therapies, management of such viral infections is primarily supportive. Therefore, a clear unmet need exists for a safe and effective treatment and prophylaxis for patients with coronavirus infections or viral hemorrhagic fever.

DESCRIPTION

Figure 1:
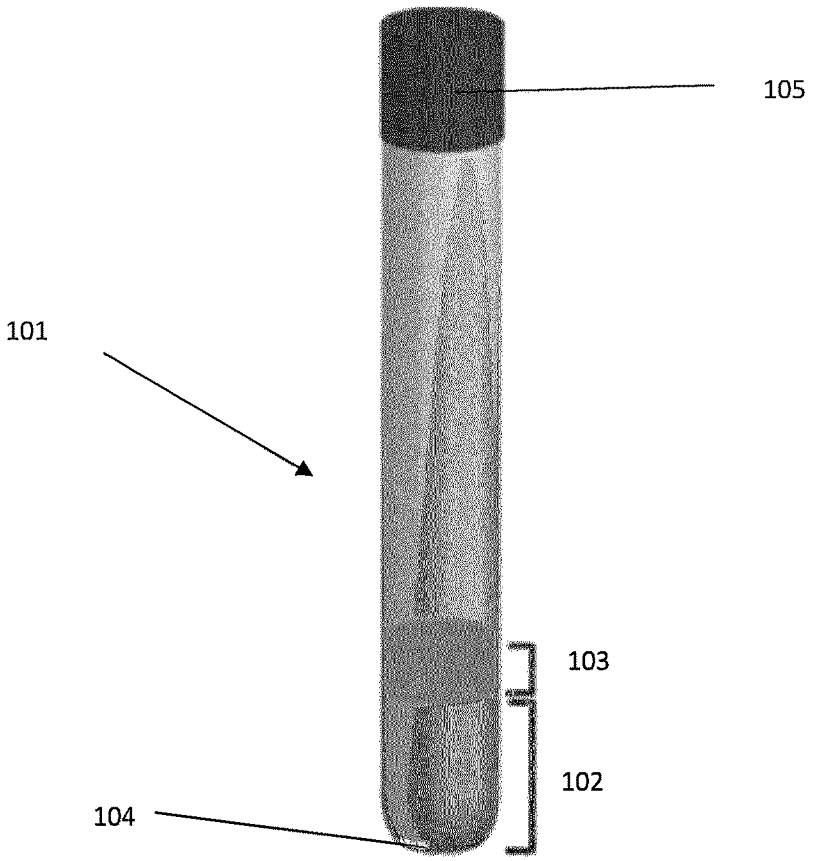
FIG. 1 illustrates a container in accordance with one embodiment of the present invention.

The devices, compositions and methods of the present invention for the safe and effective preparation of convalescent plasma or convalescent serum are useful for treating coronavirus infections (COVID-19) and viral hemorrhagic fever, and conditions associated with such infections, and include for example convalescent plasma/serum being obtained from one or more donors previously infected with the same type of virus (e.g., hyperimmune plasma, convalescent plasma) as the subject in need of treatment and prophylaxis.

The invention provides highly innovative, efficient, specific, quick and reproducible GMP medical devices to produce standardized preparations of plasma and serum obtained from one or more plasma donors previously infected with or immunized against such viruses. The plasma may be derived from donor's peripheral blood or bone marrow.

Convalescent plasma and serum for therapeutic applications should be obtained in GLP laboratories with certified devices manufactured in GMP conditions. The medical devices of the present invention fulfill these conditions. They allow the rapid preparation, by a single step centrifugation in closed circuit system, of convalescent plasma and convalescent serum.

The invention encompasses different sizes of containers, in particular centrifugation containers or centrifugation tubes, ranging from 10 ml, 20 ml, 30 ml, 40 ml, 50 ml, 100 ml, 200 ml or up to 500 ml. For a 10 ml container with 10 ml of venous blood, around 5.5 ml of plasma or 4 ml of serum is obtained. The size and number of containers/tubes collected can be adapted to reach the desired volume of final product, which the skilled artisan can determine. Advantageously, the invention provides a standardized therapeutic dose for each type of container/tube used (from 10 ml to 500 ml container) enabling the medical professional to provide the subject/patient with an effective and safe therapeutic treatment and prophylaxis without additional/numerous testing or procedure. The medical professional can easily determine the number of injections required in relation to the type of container used. Further, advantageously, the invention allows the production of the therapeutic dose in a simple, safe and non-costly process involving only one single centrifugation process, the convalescent plasma/serum is directly aspirated with a syringe and may be immediately injected (intravenous use) to the subject/patient or stored (e.g. deep freeze) for further use. Advantageously, the invention provides not only an adequate therapeutic dose but a convalescent plasma/serum that is free of cells (or with a very limited number).

The present invention comprises methods and kits intended for rapid, efficient, reliable and standardized preparation of convalescent plasma and convalescent serum from a donor's blood or bone marrow.

The devices particularly suitable for convalescent plasma and convalescent serum have the following common features:

i) Container, preferably a centrifugation tube or centrifugation syringe. Preferably, the tube is made of borosilicate. Preferably, the tube contains silicone, and is depyrogenated. Preferably, the tube is under vacuum with a stopper. A tube is herein characterized by a distal end and proximal end, with the proximal end having an aperture for the collection of material, substance or composition, e.g. whole blood or bone marrow.

ii) A complex Newtonian polymer as substance for cellular separation by gravity. Preferably, the complex Newtonian polymer is a thixotropic gel. Preferably, the thixotropic gel is a large polymer complex with mode of action dependent on the viscosity and density.

In one embodiment, the thixotropic gel is selected from one or more of: an oligomer, polymer, polyolefin hydrocarbon oligomer, an acrylic resin mixture, a PEG-Silica Gel, or any combination thereof. The thixotropic gel may be an oligomer, preferably a polyolefin hydrocarbon oligomer or an acrylic resin mixture. The thixotropic gel may be a PEG-Silica Gel.

In one embodiment, the thixotropic gel is selected from a polyoxyalkylene polyol, trioctyl trimellitate, a hydrocarbonated resin, silica dimethyl silylate, or any combination thereof.

In one embodiment, the thixotropic gel is a polyoxyalkylene polyol. The polyoxyalkylene polyol preferably comprises hydroxyl group containing groups of formula 1:

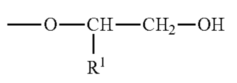

(1)

The polyoxyalkylene polyol may be selected from one or more of: polyethylene and/or polypropylene glycol trimethylolpropane ether, methyloxirane polymer with oxirane, ether with 2-ethyl-2-(hydroxymethyl)-1,3-propanediol; poly (oxyethylene and/or oxypropylene) trimethylolpropane ether, trimethylol propane, ethoxylated trimethylolpropane, propoxylated trimethylol propane, or any combination thereof. Preferably, the thixotropic gel is trioctyl trimellitate. Preferably, the thixotropic gel is a hydrocarbonated resin. Preferably, the thixotropic gel is silica dimethyl silylate.

Use of a thixotropic gel as described herein, preferably use of a polyoxyalkylene polyol, enables the collection of a plasma with very good stability. Furthermore, the time required for preparation is significantly less compared to conventional thixotropic gels and produces plasma with improved results compared to the use of conventional thixotropic gels.

The thixotropic gel may contain additional substances as, or equivalent thereof, Tris(2-ethylhexyl)benzene-1,2,4-tricarboxylate, silicon dioxide, silane, dichlorodimethyl-reaction products, and/or silica. The thixotropic gel may be further characterized by: insoluble in water, partially soluble in acetone, and easily soluble in hexane. Further, the thixotropic gel may be characterized by a viscosity of approx. 400 to 700 Pa·s at 15° C., approx. 100 to 250 Pa·s at 25° C., 30 to 100 Pa·s at 45° C. and 10 to 80 Pa·s at 65° C.

It has been determined that the following devices are particularly adapted to provide effective and safe convalescent plasma and convalescent serum.

A device containing as substance a thixotropic gel with a density of about 1.02 to about 1.05 g/cm$^3$ and an anticoagulant, herein referred to as C1-plasma. Such a device enables the collection of a highly "pure" plasma with extremely low levels of cell contamination and high level of antibodies. Preferably, the density is of about 1.03 g/cm$^3$ to about 1.04 g/cm$^3$ or 1.03 g/cm$^3$ to about 1.045 g/cm$^3$. More preferably, the density is of about 1.04 g/cm$^3$ to about 1.05 g/cm$^3$, of about 1.04 g/cm$^3$, about 1.045 g/cm$^3$ or about 1.05 g/cm$^3$. Preferably, the anticoagulant is sodium citrate, preferably at a concentration of 0.1M. Preferably, the device contains only these two substances as layers in the tube, i.e. the thixotropic gel and the anticoagulant. Preferably, the substances have been prefilled in the container. The thixotropic gel is preferably present as a first layer in the device, e.g. from the closed end of the tube (distal), followed by a second layer consisting of the anticoagulant. Advantageously, such device enables the quick preparation of convalescent plasma without Red Blood Cells (RBCs) and polynucleated cells, i.e. plasma or BMC without mononuclear white blood cells (MNC), a leukocyte-depleted plasma or BMC. Density of the gel may be about 1.055 g/cm$^3$, 1.05 g/cm$^3$, 1.045 g/cm$^3$, 1.04 g/cm$^3$, 1.035 g/cm$^3$, 1.03 g/cm$^3$, 1.025 g/cm$^3$, 1.02 g/cm$^3$, 1.015 g/cm$^3$ or 1.01 g/cm$^3$.

A device containing a thixotropic gel without an anticoagulant herein referred to as C-Serum. The thixotropic gel has a density of about 1.02 to about 1.05 g/cm$^3$, preferably about 1.03 g/cm$^3$ to about 1.04 g/cm$^3$ or 1.03 g/cm$^3$ to about 1.045 g/cm$^3$. More preferably, the density is of about 1.04 g/cm$^3$ to about 1.05 g/cm$^3$, of about 1.04 g/cm$^3$, about 1.045 g/cm$^3$ or about 1.05 g/cm$^3$. Preferably, the device (container or tube) contains also a coagulation activator as second layer (proximal) above the thixotropic gel layer (distal) and is referred to as C1-Serum. Preferably, the device contains only these two substances as layers in the tube, i.e. the thixotropic gel and the coagulation activator. Preferably, the substances have been prefilled in the container. Preferably, a calcium salt is used, without limitation, $CaCO_3$, $CaSO_4$ or $CaCl_2$. A preferred calcium salt for use in the invention is calcium gluconate (CaGL). Preferably calcium gluconate at about 1%, 2%, 3%, 4%, 5%, 6%, 7%, 8%, 9%, 10% to about 20% may be added in the container (tube) as second layer above the thixotropic gel layer. More preferably, calcium gluconate at about 10% is used. In one embodiment, calcium chloride or calcium saccharate may be used instead. In one embodiment, a combination of calcium gluconate and calcium saccharate may be used. For example, for a 100 ml of solution, about 9.5 g of Calcium gluconate and about 360 mg of Calcium saccharate may be used. The skilled artisan will easily determine the appropriate calcium content according to the specific use. The invention also encompasses a container or tube containing only a thixotropic gel as layer, herein referred to as C2-Serum. Preferably, the thixotropic gel has been prefilled in the container. Advantageously, such device enables the quick preparation of a convalescent serum. Density of the gel may be about 1.055 g/cm$^3$, 1.05 g/cm$^3$, 1.045 g/cm$^3$, 1.04 g/cm$^3$, 1.035 g/cm$^3$, 1.03 g/cm$^3$, 1.025 g/cm$^3$, 1.02 g/cm$^3$, 1.015 g/cm$^3$ or 1.01 g/cm$^3$.

The following device may also be used in the context of the present invention referred to as C2-Plasma, such device containing:

i) a thixotropic gel with a density of about 1.055 to about 1.095 g/cm$^3$ (distal), and
ii) an anticoagulant (proximal),
wherein the thixotropic gel is preferably present as a first layer in the device, e.g. from the closed end of the tube (distal), followed by a second layer consisting of the anticoagulant.

Such device contains blood mononuclear cells from the donor's blood or bone marrow, which may be useful in some infections. Preferably, the density is of about 1.08 to about 1.09 g/cm$^3$, or 1.075 to about 1.09 g/cm$^3$. Most preferably, the density is of about 1.075 to about 1.08 g/cm$^3$. Preferably, the anticoagulant is sodium citrate, preferably at a concentration of 0.1M. Preferably, the device contains only these two substances as layers in the tube, i.e. the thixotropic gel and the anticoagulant. Preferably, the substances have been prefilled in the container. Preferably, the device, for example the container, is prefilled only with thixotropic gel as a layer from the distal end of the container.

The invention also encompasses a container for the preparation of convalescent plasma or convalescent serum from blood or bone marrow for use in the treatment and/or prophylaxis of viral infections and associated conditions, wherein said container is prefilled only with an anticoagulant as layer from the distal end of said container.

Container/tubes containing a thixotropic gel and an anticoagulant are referred to a C-Plasma.

The anticoagulant in all the above devices may be at a concentration different than 0.1M, ranging from 0.05 to 0.15M, or preferably from 0.08M to 0.14M, or greater than 0.08M, preferably greater than 0.09M. Sodium citrate is a preferred anticoagulant for transfusional medicine.

The densities provided (may be referred to as gravity) have been measured at a temperature of about 25° C.

The devices (containers, tubes) may be coated with one or more substances, preferably silicone.

The convalescent plasma and convalescent serum issued from these devices can be used alone or in combination, wherein combination include:

i) C1-Plasma and C2-Plasma,
ii) C1-Plasma and C1-Serum,
iii) C1-Plasma and C2-Serum,
iv) C2-Plasma and C1-Serum,
v) C2-Plasma and C2-Serum.

The invention encompasses convalescent plasma/serum lysates obtained from any device or combination thereof.

Convalescent plasma/serum lysates may be generated by following this protocol: immediately after preparation, freeze the convalescent plasma/serum preparations down to at least −20° C. For utilization, thaw the lysate at 37° C. (water bath) until the ice clots disappear. Do not warm the lysate.

The invention encompasses the following combinations (whether in fresh, lysate or else form), but not limited to:

i) C-Plasma from blood+C-Plasma from bone marrow,
ii) C-Plasma from blood+C-Serum from bone marrow,
iii) C-Plasma from blood+C-Serum from blood,
iv) C-Plasma from bone marrow+C-Serum from bone marrow,
v) C-Plasma from bone marrow+C-Serum from blood, or
vi) C-Serum from bone marrow+C-Serum from blood.

Kits may comprise any of the combination of containers/tubes herein disclosed and with a number of containers/tubes ranging from 1 to 1000. Further the kits may contain the following additional material:

Blood collection accessory set
Horizontal head (swinging bucket) or a fixed 450 angle rotor centrifuge.

Advantageously, the devices of the invention do not induce an inflammatory reaction and avoid/reduce reactions to plasma/serum constituents, including immunological reactions such as serum sickness.

The devices may be substitute and/or combine with synthetic copolymers, ceramic and glass-ceramics, bioartificial blends of natural and synthetic materials.

In one aspect, the invention provides a composition or a device, preferably a tube or syringe, comprising or prefilled with a cell selector gel (e.g. thixotropic gel) and an anticoagulant. Preferably, the thixotropic gel is layered beneath the anticoagulant at the distal end of the tube. Tube may be characterized by a first layer of thixotropic gel followed by a second layer of anticoagulant followed with open space for the collection of a substance (e.g. whole blood, bone marrow or other substance). Density of the thixotropic gel (herein also referred to as cell selector gel or CSG) is between 1.04 and 1.09 g/cm$^3$, preferably between 1.045 g/cm$^3$ and 1.075 g/cm$^3$. Density of the gel may be 1.075 g/cm$^3$, 1.07 g/cm$^3$, 1.065 g/cm$^3$, 1.06 g/cm$^3$, 1.055 g/cm$^3$, 1.05 g/cm$^3$, 1.045 g/cm$^3$, 1.04 g/cm$^3$, 1.035 g/cm$^3$, 1.03 g/cm$^3$ or 1.025 g/cm$^3$.

In another aspect, the invention provides a composition or a device, preferably a tube or syringe, comprising or prefilled with a cell selector gel (e.g. thixotropic gel) and a coagulation activator. Preferably, the thixotropic gel is layered beneath the coagulation activator at the distal end of the tube. Tube may be characterized by a first layer of thixotropic gel followed by a second layer of coagulation activator followed with open space for the collection of a substance (e.g. whole blood, bone marrow or other substance). Density of the thixotropic gel (herein also referred to as cell selector gel or CSG) is between 1.04 and 1.09 g/cm$^3$, preferably between 1.045 g/cm$^3$ and 1.075 g/cm$^3$. Density of the gel may be 1.075 g/cm$^3$, 1.07 g/cm$^3$, 1.065 g/cm$^3$, 1.06 g/cm$^3$, 1.055 g/cm$^3$, 1.05 g/cm$^3$, 1.045 g/cm$^3$, 1.04 g/cm$^3$, 1.035 g/cm$^3$, 1.03 g/cm$^3$ or 1.025 g/cm$^3$.

In another aspect, the invention provides a composition or a device, preferably a tube or syringe, comprising or prefilled only with a cell selector gel (e.g. thixotropic gel). Preferably, the thixotropic gel is layered at the distal end of the tube. Tube may be characterized by a layer of thixotropic gel followed with open space for the collection of a substance (e.g. whole blood, bone marrow or other substance). Density of the thixotropic gel (herein also referred to as cell selector gel or CSG) is between 1.04 and 1.09 g/cm$^3$, preferably between 1.045 g/cm$^3$ and 1.075 g/cm$^3$. Density of the gel may be 1.075 g/cm$^3$, 1.07 g/cm$^3$, 1.065 g/cm$^3$, 1.06 g/cm$^3$, 1.055 g/cm$^3$, 1.05 g/cm$^3$, 1.045 g/cm$^3$, 1.04 g/cm$^3$, 1.035 g/cm$^3$, 1.03 g/cm$^3$ or 1.025 g/cm$^3$.

The kit may further comprise:

i) a collection device, optionally or preferably comprising or consisting of a collection holder with accessories, preferably or optionally a safety lock and butterfly needle, to be affixed to the container for collection of blood and/or bone marrow into said container and wherein said collection preferably or optionally occurs in closed circuit, preferably or optionally automatically, preferably or optionally by vacuum, and/or ii) a collection device to be affixed to the container for collection of convalescent plasma and/or convalescent serum, wherein said collection preferably or optionally occurs in closed circuit, preferably or optionally automatically, and/or iii) a transfer device to be affixed to the container for the transfer of convalescent plasma and/or convalescent serum into another container, wherein said container is preferably or optionally a tube or syringe, preferably or optionally under vacuum, wherein said transfer preferably or optionally occurs in closed circuit, preferably or optionally automatically, preferably or optionally by vacuum, preferably or optionally either by direct contact between the two containers or through means of a device, and/or iv) optionally wherein said device further comprises at least one filter (PALL OR DSELF-TRAINER) or substance for the separation of other blood components and/or bone marrow components, in order to remove cells from the convalescent plasma and/or convalescent serum, and/or v) the container optionally is under vacuum.

Instead or in addition to the thixotropic gel, the container may contain a filter for the removal of cells. Such filter may instead or in addition be present in a syringe, other device or a cell strainer for the collection of the convalescent plasma and/or convalescent serum.

The kit may further comprise a syringe-driven filter for collecting plasma from one or more of the containers or tubes as herein described. The syringe-driven filter is preferably operable to be in fluid communication with the one or more containers or tubes as herein described. The syringe-driven filter preferably comprises a PVDF membrane filter. The syringe-driven filter preferably comprises a 0.55 μm or lower membrane filter. For example, the membrane filter may have a membrane size of 0.55 μm, 0.54 μm, 0.53 μm, 0.52 μm, 0.51 μm, 0.50 μm, 0.49 μm, 0.48 μm, 0.47 μm, 0.46 μm, 0.45 μm or lower. Preferably the membrane filter has a membrane size of 0.45 μm or lower. It has been found that membrane size of larger than 0.55 μm leads to too great contamination levels. It has also been found that a membrane size of 0.45 μm or less provides no contamination. The membrane filter may be in the syringe to collect the plasma. The membrane filter may be in the container or tube. The membrane filter may be in the container or tube and located either above or below the thixotropic gel. The membrane filter may be in both the syringe and the container or tube. For example, the syringe may comprise a first membrane filter and the container or tube may have a second membrane filter. A first membrane filter may be provided in a first syringe and a second membrane filter may be provided in a second syringe. The first and second syringes may be used consecutively. The first membrane filter may have a different membrane size to the second membrane filter. For example, the first membrane filter may have a larger membrane size, for example 0.5 μm, than the second membrane filter, which may for example have a size of 0.45 μm.

In one embodiment, the kit comprises a container or tube for use in the treatment and/or prophylaxis of viral infections and/or associated conditions prefilled with a thixotropic gel comprising a polyoxyalkylene polyol, and a syringe-driven filter operable to be in fluid communication with the container or tube. The use of a syringe-driven filter with the container or tube of the present invention has been found to provide a very pure plasma without any cells or platelets. The kit of the present invention may be used to provide a pure rich plasma composition with useful antibodies for the prophylaxis and treatment of viral infections and/or associated conditions such as COVID-19.

For topical use, in the case of wounded patient (chronic wound, surgical wound), the container (tube or syringe) of the present invention may further contain a preservation solution, optionally or preferably plasmalyte-A, at the least one coagulation activator, thrombin serum, tricalcium phosphate (TCP), hyaluronic acid composition, calcium gluconate, calcium saccharate, chitosan, fibroin, fibroin-silk protein or fibroin proteins, growth factors, mannitol, collagen, albumin, or ascorbic acid.

In further embodiments, the invention provides the container, tube or syringe according to any of the previous aspects or embodiments further characterized in that:

a) at the least two containers, at the least one container and one syringe or at the least two syringes may be connected together through means of a connecting device enabling transfer of any substance, material, plasma, serum or else composition from one container or syringe to the other container or syringe, b) said container is a tube, and/or c) said tube or syringe allows the withdrawal of about 1 ml to about 20 ml of whole blood, bone marrow, plasma, serum, preferably or optionally about 2 ml to about 10 ml, preferably or optionally about 4 ml.

d) said container and/or syringe is sterile and/or non-pyrogenic, and/or e) said container is suitable for the preparation of convalescent plasma or convalescent serum, and/or f) said container is prefilled with or comprises from about 1 ml to about 10 ml of cell-selector gel, and/or g) said container comprises or is prefilled with about 0.2 ml to about 10 ml of anticoagulant, preferably or optionally sodium citrate, from about 2% to about 6%, preferably or optionally about 4%, and/or h) said container is prefilled:

1. during the manufacturing process and/or
2. before centrifugation, either before and/or after collection of blood or bone marrow into said container, and/or
3. with at the least one substance, biomaterial, gel and/or anticoagulant or any combination thereof and is contained in a kit or medical device.

In a further embodiment, a 10 ml tube may contain about 2.5 ml of inert cell-selector gel/thixotropic gel and optionally about 0.6 ml of anticoagulant, preferably or optionally sodium citrate at about 4%. Such tube may further contain a coagulation activator, preferably calcium gluconate.

In one embodiment, the tube or container may be used for (i) virus collection, storage and transportation tube (prior to processing) and/or (ii) antibody collection, storage and transportation tube (after processing)

The device, container or tube may further comprise a preservation solution.

In further embodiments, the invention provides a medical device or kit according to any of the previous aspects or embodiments, further comprising a piston stopper, at the least one self-adhesive disc, a luer connector, anesthetic solution, injection accessories such as needles and/or syringes, luer-lock syringes, a clip device, a trocar, ampoule of coagulation activator such as calcium chloride or calcium gluconate, a paper mask, a nozzle for spray application, a double piston stopper, an applicator syringe holder and/or a connector, or any combination thereof.

In further embodiments, the invention provides a medical device or kit according to any of the previous aspects or embodiments, further comprising a portable sterilization device for killing microorganisms on an object, in which the portable sterilization device comprises a storage compartment defining a recess to receive and store one or more objects therein, a UV light source operable to supply UV radiation within the storage compartment, and a power source in communication with the UV light source. The irradiance of the UV light source is preferably at least 20 uW/$cm^2$. Preferably, the irradiance of the UV light source is no more than 1550 uW/$cm^2$, for example no more than 1543 uW/$cm^2$.

The portable sterilization device is preferably able to provide a 99.9% sterilization rate within a sterilization time of preferably no more than 5 minutes, preferably no more than 2 minutes, for example no more than 1 minute.

The irradiance of the UV light source is preferably sufficient to kill microorganisms selected from: *Escherichia coli* and or *Staphylococcus aureus*. The irradiance of the UV light source is preferably sufficient to deodorize the one or more objects within the storage compartment.

In one embodiment, the UV light source comprises one or more UV LEDs.

The portable sterilization device may further comprise a timer in communication with the UV light source and operable to control the duration of the supply of UV radiation.

The portable sterilization device may further comprise a temperature sensor in communication with the storage compartment and operable to detect the temperature within the storage compartment.

The portable sterilization device may further comprise a moisture sensor in communication with the storage compartment and operable to detect the moisture levels within the storage compartment.

The portable sterilization device may further comprise a control system in communication with the power source and the UV light source, and optionally one or more of: a timer and/or a temperature sensor and/or moisture sensor, to control one or more of: the duration of the supply of UV light and/or the intensity of the supply of UV light and/or temperature within the storage compartment.

The portable sterilization device may further comprise one or more alert mechanisms operable to provide an audible and/or visual signal to an operator indicative of one or more of: sterilization process in operation and/or sterilization process completion. In one embodiment, the storage compartment comprises a lid operable to be moved between a first closed position in which access to the recess defined by the storage compartment is prevented, and a second open position providing access to the recess defined by the storage compartment. The device may comprise a closure mechanism operable to secure the lid in the first closed position and operable to be released to enable a user to move the lid towards the second open position. The device may further comprise a sensor configured to detect movement of the lid, or release of a closure mechanism in order to move the lid, to the second open position and operable to prevent power supply to from the power source to the UV light source when the lid is moved from the first closed position towards the second open position or on release of a closure mechanism.

The portable sterilization device may comprise a support frame configured to be received within the recess of the storage compartment, and to receive one or more objects thereon. The support frame may be configured to be removable from the recess. The one or more objects may for example be one or more containers or tubes as herein defined.

The control system of the portable sterilization device may be operable to provide a plurality of different modes of operation, for example a fast sterilizing operation to provide fast sterilization of the objects within the storage compartment; a sterilizing and deodorizing and sterile storage operation; and a sterilizing and deodorizing, drying (preferably smart drying), temperature control and sterile storage operation.

The fast sterilizing operation may provide fast sterilization of the objects within the storage compartment in less than 1 minute.

The sterilizing and deodorizing operation may provide for a 3 minute sterilization and deodorization operation and maintaining sterile storage for a predetermined time period or until the storage compartment is opened.

The sterilizing and deodorizing, drying, temperature control and sterile storage operation may comprise sterilizing and deodorizing for a period of up to 3 minutes, subsequent drying of the object(s) for a predetermined time period (for example for 1 minute) after completion of sterilization/deodorization, and maintaining sterile storage for a predetermined time period or until the storage compartment is opened. In one embodiment, the drying operation may be a smart drying operation. In particular, the control system may monitor the moisture levels within the recess of the storage compartment and may activate the drying operation until the moisture levels fall below a predetermined minimum level. In one embodiment, the drying operation may be activated for a time period, such as for example 30 seconds, 60 seconds, 90 seconds, beyond the point at which the moisture levels fall below a predetermined minimum level.

In another aspect, the invention provides at least one, two, three, four, five, six, seven, eight, nine, ten or more container(s) and/or syringe(s) according to any of the previous aspects or embodiments.

A cell selector gel may herein be referred to as an oligomer, polymer or thixotropic gel.

Other substances described herein may be combined during one or more of the steps of a manufacturing method of the invention.

In another aspect, the invention provides a method of automatically manufacturing containers or hematology tubes by means of a filling machine comprising controlled vacuum and clogging of the containers or hematology/centrifugation tubes for filling the thixotropic gel, the anticoagulant, the coagulation activator or a biomaterial such as hyaluronic acid.

Preferably, the container, tube, syringe, kit or device is for human use or human treatment and prophylaxis. In one embodiment, the container, tube, syringe, kit or device may be used for animals, or adapted for veterinary use or animal treatment and prophylaxis.

Manufacturing of the devices or use of the devices is performed under laminar flow and/or bioburden controlled.

The containers, tubes or syringes may be of different shapes and made of crystal, glass, plastic or metal. Preferably, the containers, tubes or syringes are made of plastic, preferably COP or COC, preferably without phtalates.

In another aspect, the present invention provides a method or process for the preparation of a convalescent plasma, convalescent serum or convalescent BMC, comprising the steps of:

a) Centrifuging whole blood or bone marrow in a container, preferably a tube or syringe according to the invention (e.g. C1-plasma, C2-plasma, C1-serum, C2-serum),
b) Optionally homogenizing the resulting composition and/or re-suspending, preferably by inverting the container, tube or syringe, and
c) Collecting the convalescent plasma, convalescent serum or convalescent BMC.

Preferably, the preparation involves only one centrifugation. It has been determined that one centrifugation step is appropriate to provide a safe and effective therapeutic dose. Further, in one embodiment, the method involves no homogenization/resuspension following centrifugation. Following centrifugation, cells and platelets may lie just above the thixotropic gel or even stick thereon. Avoiding homogenization/resuspension and collecting the convalescent plasma/serum directly following centrifugation will advantageously provide a convalescent plasma/serum with even less cell contamination and less platelets. Such convalescent plasma/serum is referred to a highly pure convalescent plasma/serum devoid of/free of cells and platelets.

In another embodiment, convalescent plasma/serum is collected immediately following centrifugation without homogenization/resuspension. In further embodiments, convalescent plasma/serum is collected immediately following centrifugation without homogenization/resuspension and only about ¼, ⅓, about ½, about ⅔, about ¾ or about ⅘ of the plasma/serum from the proximal end of the container/tube is collected. In another embodiment, all of the plasma/serum without a thin layer on top of the thixotropic gel is collected still without homogenization/resuspension. This yields particularly highly pure convalescent plasma/serum or highly poor platelet plasma.

For C-plasma (C1-plasma, C2-plasma), the centrifugation step is performed at a force of or about 1500 g up to about 2000 g (this speed is with a radius of about 20 cm at about 2500 to about 3000 rpm). Preferably, the centrifugation step is performed in a sufficient length of time to form a barrier between the plasma and the gel containing the erythrocytes. Preferably, centrifugation time is about 15 minutes up to about 40 minutes, preferably from about 20 minutes to about 30 minutes. In one preferred embodiment, centrifugation speed is about 1500 g with centrifugation time of about 20 minutes or about 30 minutes. Centrifugation time and speed depends on the formulation present in the device. The skilled artisan can determine the appropriate centrifugation time and speed according to the composition used.

For C-serum (C1-serum, C2-serum), the centrifugation step is performed at a force of about 1500 g during approximately 30 minutes. In a further embodiment, the centrifugation step is performed at force between about 1000 g and up to about 2000 g for a time selected from about 15 minutes up to about 40 minutes, preferably at 1500 g for a time selected from about 20 minutes up to about 35 minutes, preferably at 1500 g for about 25 minutes. When a calcium activator is used, centrifugation time is advantageously reduced, e.g. about 15-30 minutes for calcium gluconate. When a glass tube is used, centrifugation time is also advantageously reduced. When both a glass tube and a calcium activator are used, preferably calcium gluconate, the centrifugation is advantageously substantially reduced for a time of about 10-20 minutes.

In another aspect, for topical use, the present disclosure also provides a medical device herein disclosed (container, tube, syringe) used for the preparation of Platelet Rich Plasma (PRP), Platelet Rich Fibrin (PRF) or thrombin serum, e.g. for the treatment of wounds (chronic or surgical wounds).

In particular, viral infections include coronavirus infections, coronaviridae infections and viral infections provoking hemorrhagic fever and COVID-19.

It has surprisingly found that these medical devices are useful to collect antibodies from convalescent donors. The devices described in the various aspects/embodiments of the invention are particularly useful to collect a substantial amount of antibodies per ml without or with minimum cell contamination.

In another aspect, the present disclosure provides a convalescent plasma, convalescent serum, convalescent BMC obtained from any device (container, tube, syringe) or method according to any of the aspects/embodiments disclosed herein.

In another aspect, the present disclosure provides a convalescent plasma, convalescent serum, convalescent BMC obtained from any device (container, tube, syringe) or method according to any of the aspects/embodiments disclosed herein for use as drug/medicament.

In another aspect, the present disclosure provides a convalescent plasma, convalescent serum, convalescent BMC obtained from any device (container, tube, syringe) according to any of the aspects/embodiments disclosed herein for the treatment and prophylaxis of viral infections with related conditions. In particular, viral infections include coronavirus infections and viral infections provoking hemorrhagic fever.

In another aspect, the present disclosure provides a device (container, tube, syringe) according to any of the aspects/embodiments disclosed herein for the treatment and prophylaxis of viral infections with related conditions. In particular, viral infections include coronavirus infections and viral infections provoking hemorrhagic fever.

In another aspect, the present disclosure provides a method of treating a subject suffering from a coronavirus or hemorrhagic fever virus infection (e.g., viral hemorrhagic fever), comprising administering to the subject a therapeutically effective amount of a plasma (e.g. plasma preparation, plasma therapeutic, convalescent plasma) and/or serum (e.g. serum preparation, serum therapeutic, convalescent serum) wherein the convalescent plasma and/or serum is obtained from one or more donors previously infected with or immunized against the same type (e.g. same genus, same species, same subtype) of virus (i.e. same type of virus as the subject/patient) using devices for the preparation of Platelet Rich Plasma (PRP), Platelet Rich Fibrin (PRF), thrombin serum or any device of the present invention.

The invention also contemplates administering convalescent plasma/serum derived from one or more donors previously infected with another type of virus, preferably in the same virus genus, species or subtype.

In some embodiments, the coronavirus (Orthocoronavirinae or Coronavirinae) is an Alphacoronavirus (species: e.g. Human coronavirus 229E, Human coronavirus NL63, *Miniopterus* bat coronavirus 1, *Miniopterus* bat coronavirus HKU8, Porcine epidemic diarrhea virus, *Rhinolophus* bat coronavirus HKU2, *Scotophilus* bat coronavirus 512), a Betacoronavirus (species: e.g. Murine coronavirus, Betacoronavirus 1, Human coronavirus HKU1, Murine coronavirus, *Pipistrellus* bat coronavirus HKU5, *Rousettus* bat coronavirus HKU9, Severe acute respiratory syndrome-related coronavirus, Severe acute respiratory syndrome coronavirus 2, *Tylonycteris* bat coronavirus HKU4, Middle East respiratory syndrome-related coronavirus, Human coronavirus OC43, Hedgehog coronavirus 1 (EriCoV)), a Gammacoronavirus (species: e.g. Infectious bronchitis virus, *Beluga* whale coronavirus SW1, Infectious bronchitis virus) and Deltacoronavirus (species: e.g. Bulbul coronavirus HKU11, Bulbul coronavirus HKU11, Porcine coronavirus HKU15).

In particular, the coronavirus is Severe acute respiratory syndrome coronavirus 2 (SARS-CoV-2), previously known as 2019-nCoV or "novel coronavirus 2019", Middle East respiratory syndrome-related coronavirus (MERS-CoV), previously known as novel coronavirus 2012 and HCoV-EMC, Severe acute respiratory syndrome coronavirus (SARS-CoV or "SARS-classic"), Human coronavirus OC43 (HCoV-OC43), Human coronavirus HKU1, Human coronavirus NL63 (HCoV-NL63, New Haven coronavirus) and Human coronavirus 229E (HCoV-229E).

In some embodiments, the hemorrhagic fever virus is a bunyavirus, arenavirus, flavivirus or filovirus. In some embodiments, the hemorrhagic fever virus is a filovirus. In some embodiments, the filovirus is an Ebola virus (e.g., Zaire ebolavirus, Bundibugyo ebolavirus, Reston ebolavirus, Sudan ebolavirus, Tai Forest ebolavirus) or a Marburg virus. In some embodiments, the hemorrhagic fever virus is an arenavirus. In some embodiments, the arenavirus is a Lassa fever virus, a Lujo virus, an Argentine hemorrhagic fever virus (e.g., Junin virus), a Bolivian hemorrhagic fever virus (e.g., Machupo virus), a Brazilian hemorrhagic fever virus (e.g., Sabia virus), a Venezuelan hemorrhagic fever virus (e.g., Guanarito virus) or Chapare hemorrhagic fever virus. In some embodiments, the hemorrhagic fever virus is a bunyavirus. In some embodiments, the bunyavirus is a Rift Valley fever virus, Crimean-Congo hemorrhagic fever virus, a Garissa virus, a Ilesha virus or a hantavirus (e.g., Hantaan virus, Dobrava virus, Saaremaa virus, Seoul virus, Puumala virus). In some embodiments, the hemorrhagic fever virus is a flavivirus. In some embodiments, the flavivirus is a dengue fever virus, a yellow fever virus, Alkhurma homorrhagic fever virus, or a tick-borne encephalitis (e.g., Omsk hemorrhagic fever virus, Kyasanur Forest disease virus). In some embodiments, the hemorrhagic fever virus is a rhabdovirus (e.g., Bas-Congo virus, BASV).

The skilled artisan can characterize the immunoglobulins from the convalescent donors. This analysis of the convalescent plasma/serum may be performed by pooling convalescent plasma/serum from one or more donors to one receiver (subject/patient).

The invention also contemplates treating coronavirus related diseases using convalescent plasma and/or convalescent serum from one or more donors previously infected with or immunized against a different type (e.g. different genus, different species, different subtype) of coronavirus and/or hemorrhagic fever virus (i.e. different type of virus as the subject/patient), for example from coronaviruses HCoV-229E, -NL63, -OC43, and -HKU1 which continually circulates in the human population and cause respiratory infections in adults and children worldwide.

The invention also contemplates treating coronavirus related diseases using multiple convalescent plasma and/or convalescent serum from multiple donors previously infected with or immunized against different types (e.g. different genus, different species, different subtype) of coronavirus and/or hemorrhagic fever virus (i.e. different types of virus as the subject/patient and among donors). This will enable pooling different types of antibodies.

The invention also encompasses treatment and prophylaxis of animals.

In some embodiments, the plasma or serum is obtained from one or more human donors. In some embodiments, the plasma or serum is obtained from one donor. In some embodiments, the plasma or serum is obtained from at least two donors. In some embodiments, the plasma or serum component is obtained from 1-12 donors. In some embodiments, the plasma or serum is obtained from 2 donors, 3 donors, 4 donors, 5 donors, 6 donors, 7 donors, 8 donors, 9 donors, 10 donors, 11 donors or 12 donors.

In some embodiments, the plasma and/or serum comprises donor plasma/serum only of the same ABO blood group as the subject. In some embodiments, the plasma and/or serum comprises donor plasma/serum of more than one ABO blood group. In some embodiments, the plasma and/or serum comprises donor plasma/serum of blood group A and blood group B. In some embodiments, the plasma and/or serum is obtained from at least 3 donors and wherein the plasma/serum comprises donor plasma of blood group A, blood group B and blood group AB. In some embodiments, the plasma and/or serum does not contain plasma/serum of blood group O.

In some embodiments, the plasma, serum or both are frozen for storage and thawed prior to administration of the plasma/serum to the subject. In some embodiments, the plasma, serum or both are lyophilized for storage and reconstituted prior to administration of the plasma/serum to the subject.

In some embodiments, multiple plasma, multiple serum or both are administered separately to the subject. In some embodiments, multiple plasma, multiple serum or both are administered sequentially to the subject. In some embodiments, multiple plasma, multiple serum or both are administered within about 72 hours, within about 48 hours, within about 24 hours, within about 15 hours, within about 8 hours, within about 4 hours, within about 2 hours, or within about 1 hour of each other. In some embodiments, plasma is administered before serum or vice-versa. In some embodiments, the plasma or serum is adjusted (e.g., increased) relative to a dilution of the plasma/serum from a pathogen inactivation process (e.g., treated with a pathogen inactivation compound). In some embodiments, the plasma and serum are administered to the subject at about the same time. In some embodiments, the plasma and serum are mixed prior to or during administration to the subject.

Previous methods injected at the least 200 ml of plasma to the subject/patient. With the present invention, the convalescent plasma and/or serum is administered to the subject/patient in a volume (e.g., total volume, total volume of one or more units) of about 1-190 ml, about 2-100 ml, about 5-100 ml or about 50 ml or about 200-500 ml. In some embodiments, the convalescent plasma and/or serum is administered to the subject in volume of about 1-2 ml/kg body weight of the subject (e.g., weight adjusted dosing). In some embodiments, the convalescent plasma and/or serum is administered to the subject in volume of about 4-6 ml/kg body weight of the subject. In some embodiments, the convalescent plasma and/or serum is administered to the subject in volume of about 1 ml/kg, about 1.5 ml/kg, about 2 ml/kg, about 2.5 ml/kg, about 3 ml/kg, about 3.5 ml/kg, about 5 ml/kg or about 6 ml/kg body weight of the subject. In some embodiments, the convalescent plasma and/or serum is administered by infusion. In some embodiments, the convalescent plasma and/or serum is administered to the subject as one or more infusions, two or more infusions, three or more infusions or four or more infusions. In some embodiments, the convalescent plasma and/or serum may be administered intramuscularly.

In another aspect, the invention provides a convalescent plasma and/or convalescent serum obtained from a device or method of the invention. In another aspect, for topical use, the invention provides a convalescent PRP, convalescent PRF and/or convalescent thrombin serum obtained from a device or method of the invention.

In another aspect, the invention provides a convalescent plasma and/or serum for the isolated processing of (hyper) immune globulins, for the enrichment of globulins, for use in the treatment and prophylaxis of infectious diseases.

In further embodiments, the production of hyperimmune globulins may comprise the use of a hemodialyzer and/or filtration.

In another aspect, the invention provides convalescent plasma/serum/bone marrow for transfusion with viral inactivation technology (e.g. methylene blue) to ensure inactivated plasma/serum for treatment and prophylaxis use.

In another aspect, the invention provides the use of certain plasma-derived products or serum-derived products obtained from convalescent plasma and/or serum, such as intravenous immunoglobulin and alpha-1 antitrypsin, for use as treatment and prophylaxis of coronavirus related disease (e.g. COVID-19) or hemorrhagic fever disease.

In another aspect, the plasma and/or serum obtained herein is used for diagnostics purposes.

Prophylaxis is encompassed by the invention. Each instance of treatment herein mentioned may be substituted by prophylaxis.

In another aspect, the invention provides the devices of any of the aspects/embodiments for the isolation, amplification and culture/expansion of cells, especially Hematopoietic Stem Cells (HSCs) and lymphocytes, including but not limited to T lymphocytes, B lymphocytes, of which Immature, naïve, memory and regulatory B cells and plasma cells. This is particularly useful for the production of antibodies.

Further, the present invention provides a highly innovative, efficient, quick and reproducible GMP medical devices to produce standardized preparations of platelet-rich-plasma, serum or mononuclear cells from donor(s)/subject (s)/receiver(s) blood or bone marrow to be used as a substitute of fetal bovine serum (FBS) for culturing the cells, especially Hematopoietic Stem Cells (HSCs), monocytes, in particular lymphocytes, including but not limited to T lymphocytes, B lymphocytes, of which Immature, naïve, memory and regulatory B cells and plasma cells. This is useful for culturing cells derived from convalescent donors. In particular, Hematopoietic Stem Cells (HSCs), monocytes, lymphocytes, including but not limited to T lymphocytes, B lymphocytes, of which Immature, naïve, memory and regulatory B cells and plasma cells from convalescent donors may be isolated, amplified and/or cultured.

B lymphocytes (B cells) play an essential role in the humoral component of the adaptive immune response. Following exposure to a pathogen or foreign material, B cells produce and secrete antibodies that circulate through the body and bind to specific pathogens, marking them for destruction. B cells also contribute to cellular immunity by maintaining immune homeostasis, including the regulation of T lymphocyte activation and expansion. The plasma/serum compositions prepared by the containers (tubes) of the present invention, including the convalescent plasma/serum, are advantageously Xeno-Free culture media, formulated and optimized for the ex vivo culture of B lymphocytes. Unlike traditional serum-containing media (FBS), the plasma/serum compositions provide a stable and optimized culture environment, void of non-human animal-derived products, that facilitates the isolation and expansion of B cells from peripheral blood or bone marrow. This media supports target antigen-specific B cell clonogenicity as well as robust culture of mouse B cell hybridoma cell lines for antibody production. In one embodiment, the media does not contain antibiotics.

The plasma/serum medium of the invention may be used with cytokine/growth factor supplements for the ex vivo culture of monocytes, lymphocytes, B cells. Medium is compatible with monocytes, lymphocytes, B cells from multiple species (i.e., human, mouse, rabbit, and canine). The cytokine/growth factor combination used depends upon the experimental design.

The plasma/serum medium may be preferably tested at the donor level and selected to be negative for antibodies to HIV-1/2, hepatitis B surface antigen (HBsAg), and/or hepatitis C virus (HCV). All other components are advantageously animal-free.

For the isolation of the monocytes and lymphocytes, a container or device of the present invention may further contain another density gradient like Ficoll-Hypaque density gradient. A method to isolate and/or to expand lymphocytes, in particular B lymphocytes, comprises:

i) Isolating monocytes from peripheral blood or bone marrow using a container, tube or method herein disclosed [alternatively Ficoll-Hypaque density gradient centrifugation may be used],
j) Optionally isolating B lymphocytes or T lymphocytes from monocytes using available kits,
k) Optionally performing cell count,
l) Optionally expanding cells/lymphocytes in convalescent plasma/serum/bone marrow or in a plasma concentrate (PC), Bone Marrow Concentrate (BMC) or thrombin serum obtained with a container or tube herein disclosed, optionally supplemented with cell expander(s),
m) Optionally adding penicillin and/or streptomycin and/or other antibiotics,
n) Optionally incubating the cells, preferably at 37° C., 5% $CO_2$ humidified incubator with optionally supplemented cytokine(s),
o) Collecting cells, optionally following centrifugation,
p) Optionally resuspending in a convalescent plasma/serum/bone marrow or in PC/BMC/thrombin serum obtained with a container or tube herein disclosed, preferably fresh preparation and optionally supplemented with fresh cell expander(s), and
q) Optionally re-plate cells.

Fresh cytokines (i.e. IL-4, IL-5, and IL-7), alone or in combination, may be added for each expansion passage. Fresh cytokines (i.e. IL-4, IL-5, and IL-7) and cell expander(s) may be added regularly (each day, each two/three days) to improve cell viability and expansion.

Cell expansion may be performed regularly by performing cell counts using e.g. a hematocytometer or by using Resazurin. Cell purity may be determined using flow cytometry.

The invention also contemplates production of antibodies with hybridomas, with culturing hybridomas advantageously in the platelet/serum medium of the invention versus the usual HAT medium.

The present invention provides medical devices, containers and tubes herein described, for the preparation of convalescent plasma, convalescent serum, convalescent bone marrow, platelet rich plasma (PRP) or serum, to be used as cell culture media supplement in replacement of FBS for various applications in xenofree conditions, i.e. a plasma/serum medium. Cell culture with PRP has been reported in Tissue Engineering ("Autologous Platelet-Rich Plasma (CuteCell PRP) Safely Boosts In Vitro Human Fibroblast Expansion. Berndt S, Turzi A, Pittet-Cuénod B, Modarressi A. Part A. 2019 November; 25(21-22):1550-1563. PMID: 30896295.)

Advantageously, a plasma medium, serum medium or bone marrow medium according to the invention (convalescent plasma, convalescent serum, convalescent bone marrow, platelet rich plasma (PRP), bone marrow concentrate, serum and other mediums herein described) does not alter the phenotype nor the genotype of cultured cells.

Cell culture for therapeutic applications should be done in GLP laboratories with certified devices manufactured in GMP conditions. Medical devices of the present invention fulfill these conditions. They allow the rapid preparation, by a single step centrifugation in closed circuit system, of platelet rich plasma or serum. Around 5.5 ml of PRP or 4 ml of serum are obtained from 10 ml of venous blood, thus the number of blood tubes collected can be adapted to reach the desired volume of final product.

Classically, for isolating mononuclear cells from patient's blood, laboratories use a Ficoll-Paque density gradient media. This methodology is time-consuming, requires several long centrifugations and thus implies a lot of steps were the cells can be damaged.

The specific medical devices of the present invention allow a specific and quick separation of blood mononuclear cells from blood or bone marrow.

This system allows the preparation of PRP together with a donor's or subject's mononuclear white blood cells (MNC). The present invention comprises methods and kits intended for rapid, efficient, reliable and standardized preparation of PRP, serum or MNC from a patient's blood or bone marrow. These devices are also suitable for animal research, diagnostics purposes and therapy.

The devices particularly suitable for cell culture of HSCs and lymphocytes (but still may be used for platelet concentrate, PRP or BMC preparation for topical use) have the following common features:

i) Container, e.g. a tube or syringe. Preferably, the tube is made of borosilicate. Preferably, the tube contains silicone, and is depyrogenated. Preferably, the tube is under vacuum with a stopper.

ii) A complex Newtonian polymer as substance for cellular separation by gravity. Preferably, the complex Newtonian polymer is a thixotropic gel. Preferably, the thixotropic gel is a large polymer complex with mode of action dependent on the viscosity and density. Preferably, the thixotropic gel is an oligomer, preferably a polyolefin hydrocarbon oligomer or an acrylic resin mixture. The thixotropic gel may be a PEG-Silica Gel.

The thixotropic gel may contain additional substances as, or equivalent thereof, Tris(2-ethylhexyl)benzene-1,2,4-tricarboxylate, silicon dioxide, silane, dichlorodimethyl-reaction products, and/or silica. The thixotropic gel may be further characterized by: unsoluble in water, partially soluble in acetone, and easily soluble in hexane. Further, the thixotropic gel may be characterized by a viscosity of approx. 400 to 700 Pa·s at 15° C., approx. 100 to 250 Pa·s at 25° C., 30 to 100 Pa·s at 45° C. and 10 to 80 Pa·s at 65° C.

For the purpose of cell culture, in particular for HSCs and lymphocytes, it has been determined that the following devices are particularly adapted and providing unexpected and effective results.

i) A device containing as substance a thixotropic gel with a density of about 1.03 to about 1.05 g/cm$^3$, herein referred to as CC-PRP. Such a device enables the collection of a "pure" PRP. Preferably, the density is of about 1.04 to about 1.05 g/cm$^3$. The device further contains as substance an anticoagulant, preferably sodium citrate, preferably at a concentration of 0.1M. Preferably, the device contains only these two substances as layers, i.e. the thixotropic gel and the anticoagulant. The thixotropic gel is preferably present as a first layer in the device, e.g. from the closed end of the tube, followed by a second layer consisting of the anticoagulant. Preferably, the substances have been prefilled in the container. Advantageously, such device enables the quick preparation of a PC or BMC except RBCs and polynucleated cells, a PC or BMC without mononuclear white blood cells (MNC), a leukocyte-depleted PRP, PC or BMC.

ii) A device containing as substance a thixotropic gel with a density of about 1.05 to about 1.095 g/cm$^3$, herein referred to as MC-PRP. Advantageously, such device enables the specific and quick separation of blood mononuclear cells from the patient's blood or bone marrow. Advantageously, such device allows the preparation of PRP, PC or BMC together with the patient's mononuclear white blood cells (MNC), a leukocyte-rich PC, BMC or PRP. Preferably, the density is of about 1.08 to about 1.09 g/cm$^3$, or 1.075 to about 1.09 g/cm$^3$. Most preferably, the density is of about 1.075 to about 1.08 g/cm$^3$. The device further contains as substance an anticoagulant, preferably sodium citrate, preferably at a concentration of 0.1M. Preferably, the device contains only these two substances as layers, i.e. the thixotropic gel and the anticoagulant. The thixotropic gel is preferably present as a first layer in the device, e.g. from the closed end of the tube, followed by a second layer consisting of the anticoagulant. Preferably, the substances have been prefilled in the container.

iii) A device containing as substance only a thixotropic gel with a density of about 1.03 to about 1.05 g/cm$^3$, herein referred to as CC-S. Advantageously, such device enables the quick preparation of a thrombin serum. Preferably, the substance has been prefilled in the container.

iv) A device herein referred to as CC-HA containing as substances:

a. a thixotropic gel with a density of about 1.03 to about 1.05 g/cm$^3$ or as mentioned under point i) supra, b. an anticoagulant, preferably sodium citrate, preferably at a concentration of 0.1M, and c. hyaluronic acid. The hyaluronic acid may non-crosslinked or crosslinked. Preferably, the hyaluronic acid has a molecular weight of about 1500 Kda and at about 1.5% to about 2%, preferably about 2%. The hyaluronic acid may be a crosslinked hyaluronic acid obtained from a method herein described. The molecular weight might range from 500 KDa to 9000 KDa Preferably, the device contains only these three substances as layers, i.e. hyaluronic acid, the thixotropic gel and the anticoagulant. The hyaluronic acid is preferably present as a first layer in the device, e.g. from the closed end of the tube, followed by a second layer consisting of the thixotropic gel followed by a third layer consisting of the anticoagulant. Preferably, the substances have been prefilled in the container. Advantageously, such device enables the quick preparation of a PC or BMC in combination with HA. HA may be substituted by another biomaterial.

v) A device herein referred to as MC-HA containing as substances:

a) a thixotropic gel with a density of about 1.05 to about 1.09 g/$cm^3$ or as mentioned under point ii) supra, b) an anticoagulant, preferably sodium citrate, preferably at a concentration of 0.1M, and c) hyaluronic acid. The hyaluronic acid may non-crosslinked or crosslinked. Preferably, the hyaluronic acid has a molecular weight of about 1500 Kda and at about 1.5% to about 2%, preferably about 2%. The hyaluronic acid may be a crosslinked hyaluronic acid obtained from a method herein described. The molecular weight might range from 500 KDa to 9000 KDa.

Preferably, the device contains only these three substances as layers, i.e. hyaluronic acid, the thixotropic gel and the anticoagulant. The hyaluronic acid is preferably present as a first layer in the device, e.g. from the closed end of the tube, followed by a second layer consisting of the thixotropic gel followed by a third layer consisting of the anticoagulant. Preferably, the substances have been prefilled in the container. Advantageously, such device enables the quick preparation of a PC or BMC in combination with HA. HA may be substituted by another biomaterial.

The anticoagulant may be at a concentration different than 0.1M, ranging from 0.05 to 0.15M, or preferably from 0.08M to 0.14M, or greater than 0.08M, preferably greater than 0.09M.

The densities provided (may be referred to as gravity) have been measured at a temperature of about 25° C. The blood preparations issued from these devices can be used alone or in combination: The products, compositions may be used in cell therapy research/therapy.

Advantageously, the containers and tubes herein described are also useful for the preparation of PC, BMC or thrombin serum administered topically.

Combinations of the above devices in cell culture have provided unexpected results with specific advantages:

CC-S+CC-PRP: the autologous thrombin present in the CC-S will re-activate the coagulation in the PRP preparation and allows the formation of a fibrin matrix where the platelets are entrapped.

CC-S+MC-PRP: PRP: the autologous thrombin present in the CC-S will re-activate the coagulation in the PRP preparation and allows the formation of a fibrin matrix where the mononuclear cells and the platelets are entrapped.

CC-PRP+MC-PRP: To combine the PRP from two different preparations and to maximize its growth effects together with the mononuclear cells specifically isolated thanks to the MC-PRP device.

CC-HA: a single device that allows the combination of PRP and hyaluronic acid in the same preparation with given density appropriate for cell culture.

The invention encompasses platelet lysates obtained from any device or combination thereof.

From the preparations issued from CC-PRP, platelet lysates may be generated by following this protocol: immediately after preparation, freeze the PRP preparations down to at least −20° C. in the without further manipulation. For utilization, thaw human platelet lysate, herein called HPL at 37° C. (water bath) until the ice clots disappear. Do not warm the HPL.

The invention encompasses CC-PRP, MC-PRP, CC-S, CC-HA or any combination thereof obtained from blood or bone marrow.

Combinations of the Technologies

The invention encompasses the following combinations, but not limited to:

CC-PRP+MC-PRP from blood
CC-PRP+MC-PRP from bone marrow
CC-PRP+isolated cells from donor(s)/subject(s)
HPL obtained from CC-PRP+MC-PRP from blood
HPL obtained from CC-PRP+MC-PRP from bone marrow
HPL obtained from CC-PRP+isolated cells from donor(s)/subject(s)
CC-S+MC-PRP from blood
CC-S+MC-PRP from bone marrow
CC-S+isolated cells from donor(s)/subject(s)
CC-S+CC-PRP+MC-PRP from blood
CC-S+CC-PRP+MC-PRP from bone marrow
CC-S+CC-PRP+isolated cells from donor(s)/subject(s)
CC-HA+MC-PRP from blood
CC-HA+MC-PRP from bone marrow
CC-HA+isolated cells from donor(s)/subject(s)
MC-HA+MC-PRP from blood
MC-HA+MC-PRP from bone marrow
MC-HA+isolated cells from donor(s)/subject(s)

Autologous or allogenic PRP may be used for the cell culture.

Further, an albumin gel may be used as support or matrix for the cell culture. The albumin gel may be used in a single layer or dual layers with the cell culture medium in the middle (sandwich like).

In some embodiments, the level of viral infection (e.g., viral load, virus titer) in the subject is reduced. In some embodiments, the level of viral infection is reduced at least 1 log, at least 2 logs, at least 3 logs, at least 4 logs, at least 5 logs or at least 6 or more logs. In some embodiments, the level of viral infection is reduced to no detectable virus in blood of the subject. In some embodiments, the viral infection is reduced in the subject's blood below the limit of detection by nucleic acid testing. In some embodiments, nucleic acid testing is by PCR (e.g., RT-PCR). In some embodiments, the mortality associated with the virus infection is reduced. In some embodiments, the number of co-morbidities or seventy of morbidity (e.g., severity of one or more morbidities) is reduced (e.g., decreased, ameliorated). In some embodiments, the absence of clinical symptoms indicative of viral disease is achieved. In some embodiments, coagulopathy associated with the virus infection is reduced. In some embodiments, endothelial cell dysfunction (e.g., damage) associated with the virus infection is decreased. In some embodiments, endothelial cell function (e.g., associated with damage from the virus infection) is restored (e.g., partially restored). In some embodiments, endothelial barrier function is enhanced. In some embodiments, time of hospitalization is reduced. In some embodiments, time spent in ICU (e.g., intensive care, an intensive care unit) is reduced. In some embodiments, total duration and/or frequency of dialysis is decreased. In some embodiments, time on assisted ventilation is decreased. In some embodiments, incidence of organ failure is reduced. In some embodiments, multifocal necrosis (e.g., multifocal hepatic necrosis) associated with virus infection is reduced.

In some embodiments, the convalescent plasma/serum is a concentrated (e.g., purified) immunoglobulin preparation or cryoprecipitate. In some embodiments, the method further comprises treating the convalescent plasma/serum with a pathogen inactivation compound to inactivate pathogens, if present.

In some embodiments, the donor convalescent plasma/serum obtained from one or more donors previously infected with or immunized against the virus is obtained only from donors with no clinical symptoms of infection (e.g., infection with the coronavirus) with the virus at the time of donating blood. In some embodiments, the donor convalescent plasma/serum obtained from one or more donors previously infected with or immunized against the virus is obtained only from donors that have no detectable levels of the virus in their (i.e., the donor's) blood at the time of donating blood.

In some embodiments, the plasma/serum or donor convalescent plasma/serum is frozen for storage and thawed prior to administration of the plasma to the subject. In some embodiments, the plasma/serum or donor convalescent plasma/serum is lyophilized for storage and reconstituted prior to administration of the convalescent plasma/serum to the subject. In some embodiments, plasma/serum or donor convalescent plasma/serum is a concentrated (e.g., purified) immunoglobulin preparation. In some embodiments, the donor plasma/serum is obtained from the one or more donors by apheresis.

In some embodiments, the container or tube comprises a thixotropic gel and/or anticoagulant, wherein said thixotropic gel comprises trioctyl trimellitate, silica, hydrocarbon resin, polyol, phenol(s) and phosphite ester.

In some embodiments, the trioctyl trimellitate is Tris (2 ethylhexyl), said silica is Dimethyl dichlorosilane, said hydrocarbon resin is Cycloaliphatic hydrocarbon Resin, said polyol is Polyalkylene Polyol, said phenol(s) is Tetrakis (3-(3,5-di-tert-butyl-4-hydroxyphenyl) propionate of pentaerythritol) and said phosphite ester is Phosphite of tris (2,4-di-tert-butylphenyle).

In some embodiments, the container or tube comprises a thixotropic gel and/or anticoagulant, wherein said thixotropic gel comprises trioctyl trimellitate, silica, hydrocarbon resin and polyol, further optionally phenol(s) and/or phosphite ester.

In some embodiments, the thixotropic gel comprises trioctyl trimellitate in the range of 40-60%, silica in the range of 2-10%, hydrocarbon resin in the range of 30-60%, polyol in the range of 1-5%, phenol(s) in the range of 0-1% and phosphite ester in the range of 0% to 0.06%.

In some embodiments, the thixotropic gel comprises trioctyl trimellitate at about 50.96%, silica at about 4.21%, hydrocarbon resin at about 43%, polyol at about 1.73%, phenol(s) at about 0.05% and phosphite ester at about 0.05%.

In some embodiments, the container or tube comprises a thixotropic gel and/or anticoagulant, wherein said thixotropic gel comprises trioctyl trimellitate, silica, hydrocarbon resin, azelate ester and phosphite ester.

In some embodiments, the trioctyl trimellitate is Tris (2 ethylhexyl), said silica is Dimethyl dichlorosilane, said hydrocarbon resin is Cycloaliphatic hydrocarbon Resin, said azelate esters is Azelate de bis (2-éthylhexyle), and said phenol(s) is Tetrakis (3-(3,5-di-tert-butyl-4-hydroxyphenyl) propionate of pentaerythritol).

In some embodiments, the thixotropic gel comprises trioctyl trimellitate in the range of 35-55%, silica in the range of 2-10%, hydrocarbon resin in the range of 20-40%, azelate esters in the range of 10-30%, and phenol(s) in the range of 0-1%.

In some embodiments, the thixotropic gel comprises trioctyl trimellitate at about 50.96%, silica at about 4.21%, hydrocarbon resin at about 43%, azelate esters at about 15.82%, and phenol(s) at about 0.05%.

Embodiments of the present invention will now be described in more detail with reference to the accompanying Figures and Example:

Example 1

The recovery of IgG-SARS-CoV-2 is determined by withdrawing 200 ml of donor's blood from the antecubital vein of a patient with 10 tubes comprising a thixotropic gel having a density of about 1.04 g/ml to about 1.05 g/ml. One embodiment of such tubes is shown in FIG. 1. The tube 101 comprises a thixotropic gel 102 and an anticoagulant. The thixotropic gel 102 is the first layer from the distal end 104 of said tube 101, followed by a second layer consisting of said anticoagulant 103. The tube 101 is under vacuum with a stopper 105.

Figure 2:
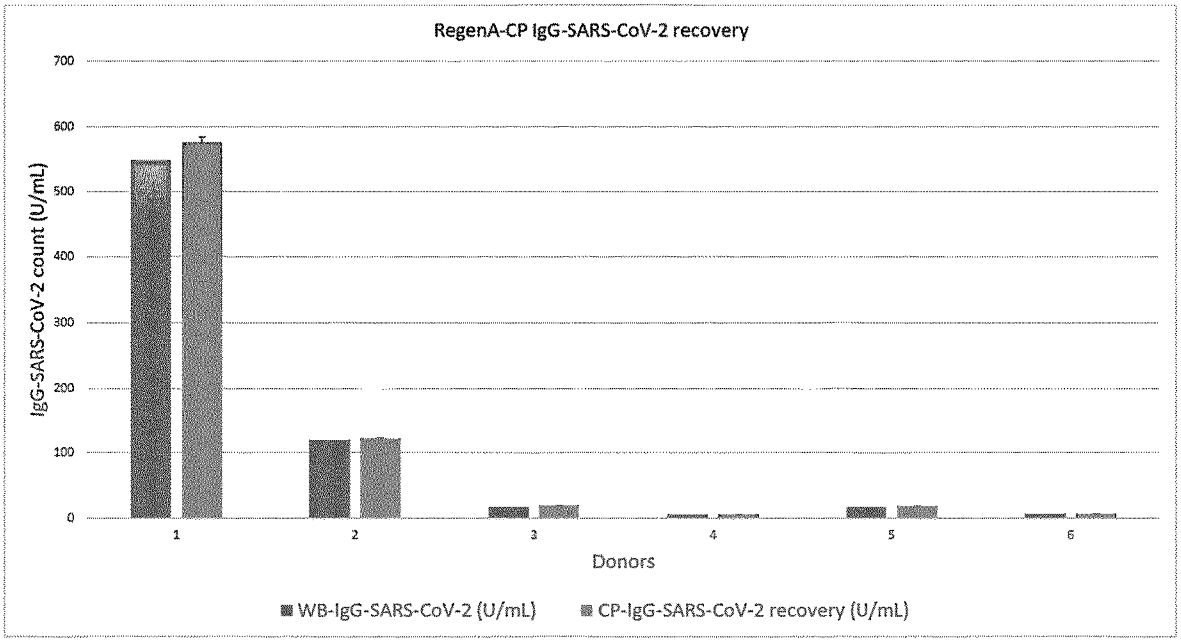
FIG. 2 illustrates the results of IgG-SARS-CoV-2 recovery.

The tubes are then centrifuged for 20 minutes at 1500 g (3400 rpm). The tubes are then removed from the centrifuge and placed vertically in a rack without inverting the tubes. A syringe-driven filter is provided in the form of a 10 ml syringe connected to a 0.45 μm filter. The syringe-driven filter is connected to a single bevel cannula that extends through the stopper of the tubes. 10 ml of convalescent plasma is then collected in a standardized manner whilst avoiding touching the separating thixotropic gel. SARS-CoV-2, Anti-S Ig, Electro Chemi-Luminescence Immuno Assay (ECLIA) tests were performed for the recovery of the IgG-SARS-CoV-2 in the convalescent plasma and the whole blood in order to determine IgG-SARS-CoV-2 recovery. The results are shown in FIG. 2 and Table 1. A cell recovery study was performed repeated with 7 donors. The result of cell recovery is shown in Table 2.

TABLE 1

| Recovery IgG-SARS-CoV-2 | | | | | | | |
|---|---|---|---|---|---|---|---|
| Donor | WB-IgG-SARS-CoV-2 (U/mL) | IgG-SARS-CoV-2_CP1 (U/mL) | IgG-SARS-CoV-2_CP2 (U/mL) | IgG-SARS-CoV-2_CP3 (U/mL) | CP-IgG-SARS-CoV-2 recovery (U/mL) | Std Dev. | % recovery |
| 1 | 547 | 572 | 570 | 583 | 575 | 7 | 105.12 |
| 2 | 120 | 123 | 122 | 122 | 122.33 | 0.58 | 101.94 |
| 3 | 17.7 | 19.2 | | 19.3 | 19.25 | 0.07 | 108.76 |
| 4 | 6 | 5.95 | 5.87 | 6.02 | 5.95 | 0.08 | 99.11 |
| 5 | 17.6 | 18.4 | 18.6 | 17.9 | 18.3 | 0.36 | 103.98 |
| 6 | 6.93 | 7.27 | 6.99 | 6.29 | 6.85 | 0.50 | 98.85 |

TABLE 2

| Cells recovery in 7 donors with described tubes | | | | | | | | | | | |
|---|---|---|---|---|---|---|---|---|---|---|---|
| | | WBC (10^3/uL) | RBC (10^6/uL) | HGB (g/L) | HCT (%) | PLT (10^3/uL) | NEUT# (10^3/uL) | LYMPH# (10^3/uL) | MONO# (10^3/uL) | EO# (10^3/uL) | BASO# (10^3/uL) |
| D 1 | WB | 6.96 | 3.92 | 122 | 35.8 | 243 | 4.74 | 1.61 | 0.52 | 0.08 | 0.01 |
| | CP | 0 | 0 | 1 | 0 | 0.333 | 0 | 0 | 0 | 0 | 0 |
| D 2 | WB | 9.99 | 4.9 | 160 | 46.2 | 297 | 6.83 | 1.87 | 0.95 | 0.31 | 0.03 |
| | CP | 0 | 0 | 1 | 0 | 0 | 0 | 0 | 0 | 0 | 0 |
| D 3 | WB | 4.53 | 4.07 | 127 | 37.5 | 147 | 2.6 | 1.12 | 0.34 | 0.41 | 0.06 |
| | CP | 0 | 0 | 0 | 0 | 0 | 0 | 0 | 0 | 0 | 0 |
| D 4 | WB | 3.82 | 4.01 | 116 | 35.60 | 263 | 1.65 | 1.70 | 0.39 | 0.04 | 0.04 |
| | CP | 0 | 0 | 0 | 0 | 0 | 0 | 0 | 0 | 0 | 0 |
| D 5 | WB | 6.36 | 4.307 | 135 | 37.567 | 147.667 | 3.123 | 2.24 | 0.48 | 0.44 | 0.08 |
| | CP | 0.004 | 0 | 0.111 | 0 | 0 | 0 | 0 | 0 | 0 | 0 |
| D 6 | WB | 5.597 | 4.627 | 143.667 | 42.633 | 175 | 3.287 | 1.56 | 0.52 | 0.207 | 0.023 |
| | CP | 0.002 | 0 | 0 | 0 | 0 | 0 | 0 | 0 | 0 | 0 |
| D 7 | WB | 5.9 | 4.37 | 130.333 | 37.533 | 144 | 3.45 | 1.77 | 0.457 | 0.2 | 0.023 |
| | CP | 0 | 0 | 0.444 | 0 | 1.444 | 0 | 0 | 0 | 0 | 0 |

Dx: Donor X;
WB: Whole Blood;
CP: Convalescent Plasma;
WBC: White Blood Cells;
RBC: Red Blood Cells;
HGB: Hemoglobin;
HCT: Hematocrit;
PLT: Platelet;
NEUT: Neutrophils;
LYMPH: Lymphocytes;
MONO: Monocytes;
EO: Eosinophiles;
Baso: Basophiles The results demonstrate the efficacy of the containers of the present invention for stable, acellular plasma collection. The containers can be used to reliably obtain almost 100% of IgG-SARS-CoV2.

In some embodiments, the level of binding activity of the virus specific antibody in the donor convalescent plasma/serum obtained from one or more donors previously infected with or immunized against the virus, after treatment with the pathogen inactivation compound, is at least 8000 of the level of binding activity of the virus specific antibody before treatment with the pathogen inactivation compound or at least 50%, 60%, 70%, 90% or 95%.

Example 2

Table 3 provides the composition of a thixotropic gel-containing formulation present within a container according to an embodiment of the present invention. The thixotropic gel-containing formulation according to one embodiment of the present invention may contain: trioctyl trimellitate (40-60% wt), silica (2-10% wt), hydrocarbon resin (30-60% wt), polyol (1-5% wt), phenols of pentaerythritol (0.01-1% wt) and phosphite esters (0.05% wt).

TABLE 3

| Brand Name | Chemical Name | Category | Spec | Range |
|---|---|---|---|---|
| TOTM | Tris (2 ethyhexyl) | trioctyl trimellitate | 50.96% | 40-60% |
| Aerosil R974 | Dimethtyl dichlorosilane | Silica | 4.21% | 2-10% |
| Escorez 5300 | Cycloaliphatic hydrocarbon Resin | Hydrocarbon Resin | 43% | 30-60% |
| Pluriol V10 | Polyalkylene Polyol | Polyol | 1.73% | 1-5% |
| Irganox | Tetrakis (3-(3,5- | Phenols, | 0.05% | 0.01-1% |

TABLE 3-continued

| Brand Name | Chemical Name | Category | Spec | Range |
|---|---|---|---|---|
| 1010 | di-tert-butyl-4-hydroxyphenyl) propionate de pentaerythritol) | pentaerythritol | | |
| Irgafos 168 | Phosphite of tris (2,4-di-tert-butylphenyle) | Phosphite ester | 0.05% | 0.05% |

Example 3

Table 4 provides the composition of a thixotropic gel-containing formulation present within a container according to an embodiment of the present invention. The thixotropic gel-containing formulation according to one embodiment of the present invention may contain: trioctyl trimellitate (35-55% wt), silica (2-10% wt), cycloaliphatic hydrocarbon resin (10-30% wt), azelate esters (10-30% wt), phenols of pentaerythritol (0.01-1% wt).

TABLE 4

| Brand Name | Chemical Name | Category | Spec | Range |
|---|---|---|---|---|
| TOTM | Tris (2 ethyhexyl) | trioctyl trimellitate | 50.96% | 35-55% |
| Aerosil R974 | Dimethtyl dichlorosilane | Silica | 4.21% | 2-10% |
| Escorez 5300 | Cycloaliphatic hydrocarbon Resin | Hydrocarbon Resin | 43% | 20-40% |
| Plastolein | bis (2-ethylhexyl) azelate | Azelate Esters | 15.82% | 10-30% |
| Irganox 1010 | Tetrakis (3-(3,5-di-tert-butyl- | Phenols, pentaerythritol | 0.05% | 0.01-1% |

TABLE 4-continued

| Brand Name | Chemical Name | Category | Spec | Range |
|---|---|---|---|---|
| | 4-hydroxyphenyl) propionate of pentaerythritol) | | | |

From examples 2 and 3, it can be seen that according to embodiments of the present invention the thixotropic gel-containing formulation contains at least 30% wt, preferably at least 35% wt, for example at least 40% wt of thixotropic gel, for example trioctyl trimellitate. In one embodiment, the thixotropic gel-containing formulation contains no more than 60% wt, preferably no more than 55% wt, for example about 50% wt thixotropic gel, for example trioctyl trimellitate. In one embodiment, the thixotropic gel containing formulation contains between 30% wt and 60% wt, preferably between 35% wt and 60% wt, preferably between 40% and 55% wt, preferably between 45% wt and 55% wt, for example about 50% wt of thixotropic gel, for example trioctyl trimellitate.

In one embodiment, the thixotropic gel containing formulation contains at least 2% wt silica, preferably at least 3% wt, preferably at least 4% wt of silica. The thixotropic gel containing formulation preferably contains no more than 10% wt, preferably no more than 8% wt, preferably no more than 5% wt of silica. In one embodiment, the thixotropic gel-containing formulation contains between 2% and 10% wt, preferably between 3% and 8% wt, preferably between 4% and 8% wt, preferably between 4% and 5% wt of silica.

In one embodiment, the thixotropic gel containing formulation contains at least 20% wt, preferably at least 30% wt of hydrocarbon resin. In one embodiment, the thixotropic gel containing formulation contains no more than 60% wt, preferably no more than 50% wt, preferably no more than 40% wt hydrocarbon resin. In one embodiment, the thixotropic gel containing formulation contains between 20% and 60%, preferably between 30% and 60%, preferably between 30% and 50% wt of hydrocarbon resin.

In one embodiment, the thixotropic gel containing formulation contains at least 0.01% wt, preferably at least 0.02% wt phenols pentaerythritol. In one embodiment, the thixotropic gel containing formulation contains no more than 1% wt, preferably no more than 0.5% wt, preferably no more than 0.1% wt phenols pentaerythritol. In one embodiment, the thixotropic gel containing formulation contains between 0.01% and 1% wt, preferably between 0.02% and 0.5% wt, preferably between 0.02 and 0.10% wt phenols pentaerythritol.

In one embodiment, the thixotropic gel containing formulation optionally contains at least 1% wt, preferably at least 1.5% wt polyol. In one embodiment, the thixotropic gel containing formulation contains no more than 5% wt, preferably no more than 3% wt, preferably no more than 2% wt polyol. In one embodiment, the thixotropic gel containing formulation contains between 1% and 5% wt, preferably between 1% and 3% wt, preferably between 1.5 and 2% wt polyol.

In one embodiment, the thixotropic gel containing formulation contains at least 10% wt, preferably at least 12% wt azelate ester. In one embodiment, the thixotropic gel containing formulation contains no more than 30% wt, preferably no more than 20% wt azelate ester. In one embodiment, the thixotropic gel containing formulation contains between 10% and 30% wt, preferably between 12% and 20% wt azelate ester.

Figure 3:
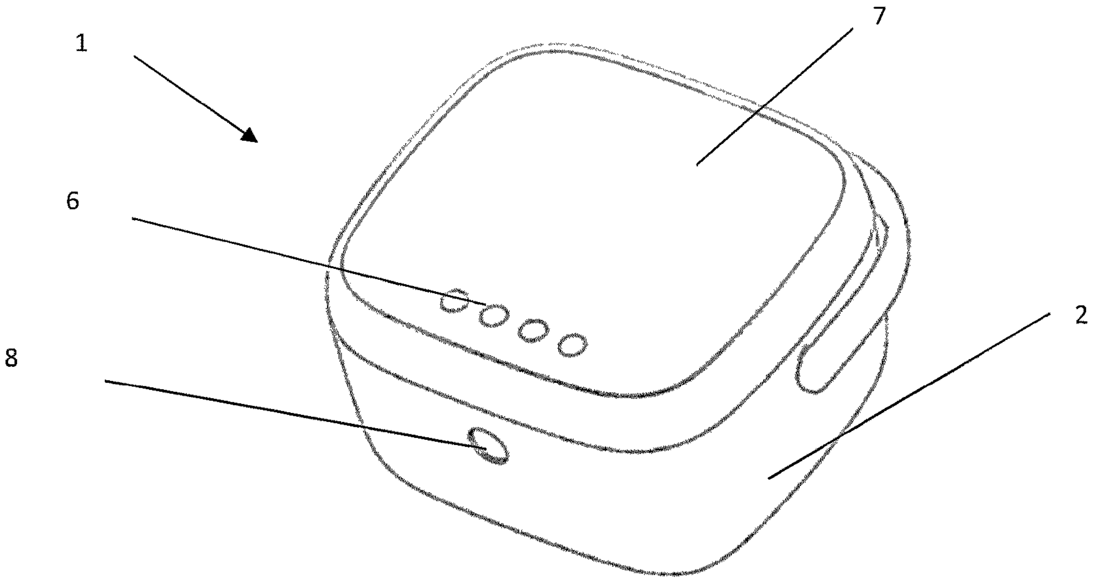
FIG. 3 is a schematic illustration of a portable sanitization device in a first closed position of a kit according to one embodiment of the present invention.
Figure 4:
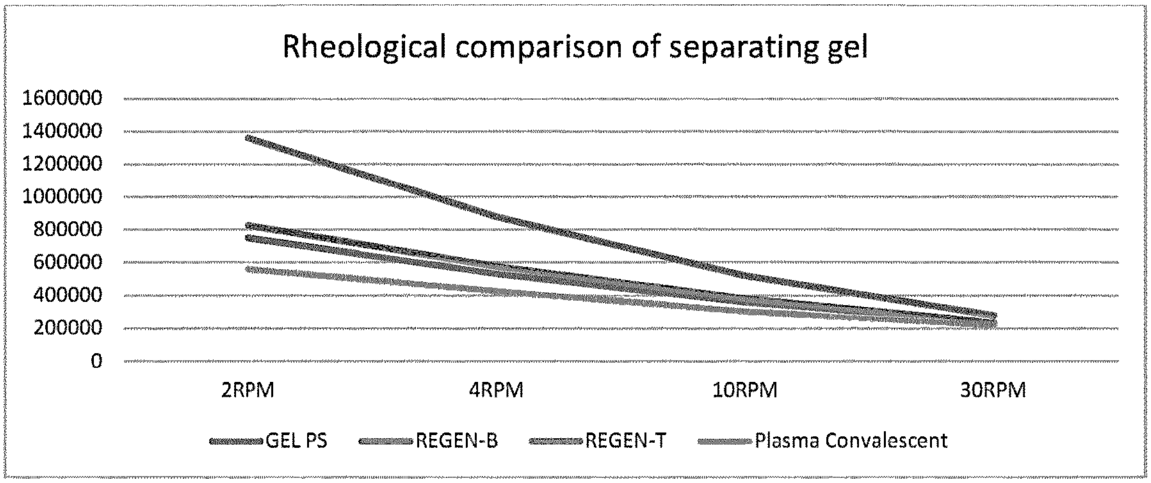
FIG. 4 is a graph illustrating the rheological comparison of a gel according to one embodiment of the present invention ("Plasma convalescent") compared to conventional gels ("Gel PS"; "REGEN-T"; "REGEN-B").

With reference to FIGS. 3 and 4, the portable sterilization device 1 of the present invention is operable to kill microorganisms on an object. The device 1 comprises a storage compartment 2 defining a recess 3 to receive and store one or more objects therein, a UV light source operable to supply UV radiation within the storage compartment, and a power source in communication with the UV light source. The irradiance of the UV light source is in the range of between 20 $uW/cm^2$ and 1543 $uW/cm^2$.

The portable sterilization device 1 comprises a support frame 4 configured to be received within the recess 3 of the storage compartment 2, and to receive one or more objects 5 thereon. In the illustrated embodiment, the support frame 4 is a rack which can be removed from the recess 3 and storage compartment 2. The objections 5 may for example be one or more containers or tubes as herein defined.

The portable sterilization device 1 further comprises a control system 6 in communication with the power source and the UV light source, a timer, a temperature sensor and a moisture sensor, to control: the duration of the supply of UV light, the intensity of the supply of UV light, temperature and moisture levels within the storage compartment.

The portable sterilization device 1 also comprises an alert mechanism operable to provide an audible and/or visual signal to an operator indicative of one or more of: sterilization process in operation and/or sterilization process completion.

The storage compartment 2 comprises a lid 7 operable to be moved between a first closed position in which access to the recess 3 defined by the storage compartment 2 is prevented, and a second open position providing access to the recess 3 defined by the storage compartment 2. The device 1 comprises a push button closure mechanism 8 operable to secure the lid in the first closed position and operable to be released to enable a user to move the lid towards the second open position. The device further comprises a sensor configured to detect movement of the lid 7 and/or release of the closure mechanism 8 in order to move the lid 7 to the second open position. The sensor is operable to prevent power supply from the power source to the UV light source when the lid is moved from the first closed position towards the second open position or on release of a closure mechanism.

In use, the user places the device 1 in the first open position (FIG. 3) and places one or more objects, for example one or more containers or tubes as herein described, on the support frame 4 within recess 3 of the storage compartment 2. The user closes lid 7 and operates the control system 6 to select the desired sterilizing programme. Once activated, the device 1 supplies UV radiation from the UV source to the objects within the recess 3 of the storage compartment 2. Exposure of the objects to UV radiation is controlled by the control panel and the selected program. The temperature and moisture sensors detect the corresponding temperature and moisture levels within the recess. The control system monitors these levels to determine when the selected program is complete in order to provide effective sterilisation and deodorisation of the objects within the recess.

The portable sterilization device 1 is able to provide a 99.9% sterilization rate within a sterilization time of preferably no more than 5 minutes, preferably no more than 2 minutes, for example no more than 1 minute. The irradiance of the UV light source is sufficient to kill microorganisms selected from: *Ischerichia coli* and or *Staphylococcus*

*aureus*. The irradiance of the UV light source is sufficient to deodorize the one or more objects within the storage compartment.

On completion of the program, the device 1 provides an alert signal, in the form of for example audible beeps and/or illuminated LEDs on an external surface of the storage compartment indicating to the user that the objects have been sterilised.

Example 4

The objective of was to produce a thixotropic gel (using the components shown in Table 5) with a density close to or less than 1.04 g/ml, which can create an isolation between blood plasma and blood cells after centrifugation in order to obtain a plasma containing as few platelets as possible. The plasma should be stable in 20 ml tubes (i.e. show no signs of leakage before and after sterilization.)

TABLE 5

| Component |
|---|
| Tris(2-ethylhexyl) (Solvent) |
| Dimethtyl dichlorosilane (Silica) |
| Cycloaliphatic hydrocarbon Resin (Polymer) |
| Phosphite of tris (2,4-di-tert-butylphenyle) (Antioxidant) |
| Tetrakis (3-(3,5-di-tert-butyl-4-hydroxyphenyl) propionate de pentaerythritol) (Anitoxidant) |
| Polyalkylene Polyol |

A thixotropic-gel was prepared with a density of less than 1.07 g/ml by reducing the amount of silica present compared to a comparative base formulation (table 6). A polyalkylene polyol, for example polyalkylene glycol, was also added as a thickener to improve strength and compensate for the lower silica content and readjusted the amount of polymer.

Comparative Base Formulation ("Regen B Gel"):

TABLE 6

| Quantity Component | Tris(2-ethylhexyl) Solvent | Dimethtyl dichlorosilane Silica | Cycloaliphatic hydrocarbon Resin Polymer | Tetrakis (3-(3,5-di-tert-butyl-4-hydroxyphenyl) propionate de pentaerythritol) Antioxidant | Phosphite of tris (2, 4-di-tert-butylphenyle) Antioxidant |
|---|---|---|---|---|---|
| 221.98 g<br>100% | 117.71 g<br>53.02% | 14.75 g<br>6.64% | 89.30 g<br>40.22% | 0.11 g<br>0.05% | 0.11 g<br>0.05% |

The thixotropic gel according to an embodiment of the present invention is shown in Table 7:

TABLE 7

| Quantity Component | Tris(2-ethylhexyl) Solvent | Dimethtyl dichlorosilane Silica | Cycloaliphatic hydrocarbon Resin Polymer | Polyalkylene polyol Thickener | Tetrakis (3-(3,5-di-tert-butyl-4-hydroxyphenyl) propionate depentaerythritol) Anitoxidant | Phosphite of tris (2,4-di-tert-butylphenyle) Antioxidant |
|---|---|---|---|---|---|---|
| 230.96 g<br>100% | 117.71 g<br>50.96% | 9.73 g<br>4.21% | 99.30 g<br>43% | 4 g<br>1.73% | 0.11 g<br>0.05% | 0.11 g<br>0.05% |

The formulation of Table 7 was prepared according to the procedure shown in Table 8.

TABLE 8

| Time | T° C. Ins | T° C. Out | Actions | Comments |
|---|---|---|---|---|
| 11 h 10 | T° ambient | N/A | Introduction of solvent117.71 g Heating start + Rotor | N/A |
| 11 h 30 | 132° C. | N/A | Add 99.30 g Polymer | Dissolution of the polymer quite fast. |
| 12 h 00 | 134° C. | N/A | Add 9.73 g Dimethtyl dichlorosilane | Presence of Dimethtyl dichlorosilane aggregates that disperse easily. |
| 13 H 00 | 133° C. | N/A | Add 4 g Polyalkylene polyol | 10 minutes after introduction, observation of a thickening of the solution. |
| 14 H 00 | 134° C. | N/A | Add 0.11 g of a first antioxidant; Add 0.11 g of a second antioxidant | N/A |
| 15 H 30 | 135° C. | N/A | End of mixing and transfer to a glass jar | Homogeneous translucent white gel |

The formulation provided a white thixotropic gel with a sticky texture and a density between 1.04 g/ml and 1.045 g/ml. The addition of the thickening agent Polyalkylene polyol, for example polyalkylene glycol, considerably increases the stability of the gel when poured into a 20 ml tube.

Example 5

A flow test was carried out to compare the stability of the gel of the present invention (Convalescent plasma gel) with two other products which are in the same gel category in terms of density, the PS gel and the Regen-B Gel ("Regengel B" as shown in Table 6). Each gel was filled into three 20 ml tubes which were horizontally coated without centrifugation or gel plating.

The flow test results are shown in Table 9:

TABLE 9

| Type de gel | Flow Test after 3 days (mm) | Flow Test after 13 days (mm) | Flow Test after 18 days (mm) |
|---|---|---|---|
| Gel PS | 4 | 10 | 14 |
| Gel PS | 3 | 9 | 15 |
| Gel PS | 4 | 11 | 14 |
| Regengel-B | 9 | 15 | 19 |
| Regengel-B | 8 | 16 | 17 |
| Regengel-B | 10 | 17 | 18 |
| Convalescent plasma gel | 0 | 0 | 0 |
| Convalescent plasma gel | 0 | 0 | 0 |
| Convalescent plasma gel | 0 | 0 | 0 |

The results obtained from the flow tests clearly demonstrate that the plasma convalescent gel of the present invention has a significantly higher stability as it has zero flow compared to the other two gels. This test also showed that the addition of Polyalkylene polyol, for example polyalkylene glycol, significantly improves the gel's stability in the tubes.

Example 6

Rheology tests were conducted to illustrate comparative viscosity measurements between convalescent plasma gel according to one embodiment of the present invention and comparative gels: PS Gel, Regen-B and Regen-T gels, using the Brookfield RV DII+ viscometer and the TF96 spindle. The data obtained are the results of 4 measurement points tested on each gel. The results are shown in FIG. 5.

FIG. 4 illustrates that the convalescent plasma gel according to one embodiment of the present invention has the lowest viscosity. This information in addition to the results from the flow test (Example 5), illustrates that the gel of the present invention has zero flow compared to the comparative gels, demonstrates that viscosity alone is not the most important factor for the gel's resistance and stability.

Example 7

A blood separation test was carried out to compare the convalescent plasma gel of Table 7/Example 4 ("Plasma Convalescent gel") with comparative gels, the PS gel and the Regen-B gel.

Each gel was filled into a 20 ml tube. The three tubes contain 6 g of gel and 2 ml of sodium citrate and 20 ml of vacuum. The tubes were then steam sterilized. Then three blood samples were taken, one per type from the same donor. Finally, the three tubes were placed in a centrifuge for 20 min. Each plasma obtained was tested without resuspension on the Syxmex XN-350 cell counter.

The results are shown in Table 10:

TABLE 10

| Recovery Results | | | |
|---|---|---|---|
| Parameters | Plasma convalescent Gel | Regen-B | PS Gel |
| Platelets | 34/10^3 uL | 232/10^3 uL | 180/10^3 uL |
| Red blood cell | 0.40/10^3 uL | 0.02/10^3 uL | 0.01/10^3 uL |
| White blood Cell | 0/10^3 uL | 2.07/10^3 uL | 0.11/10^ uL |

The results of the cell count test after blood separation on the three different gels as shown in Table 10 show that the convalescent plasma gel of the present invention removes more platelets than the comparative gels after a 20 min centrifugation without re-suspension of the plasma.

It is considered that as the density of the gel of the present invention was very close to that of the platelets this may have influenced the amount recovered. The presence of the polyalkylene polyol, for example polyalkylene glycol, may have resulted in some of the recovery being filtered out or adhering to the gel surface due to the sticky texture of the Polyalkylene polyol within the formulation.

The present invention has been found to provide a gel with a lower density than conventional gels (for example the comparative gels referred to herein) which have a density of around 1.065 g/ml, whilst also having improved stabilizing properties. The present invention provided a gel with a lower density and improved stability by reducing the silica content and by introducing polyalkylene polyol, for example polyalkylene glycol, which has intrinsic lubricating and thickening properties. The polyalkylene polyol component resulted in compensating for the decrease in silica content whilst also enabling the gel to have low density and viscosity. Furthermore, it was found that the presence of the polyalkylene polyol component also aided a significant part of the blood platelets after centrifugation due to its texture.

Example 8

A further embodiment of the gel of the present invention was provided using the components shown in Table 11.

TABLE 11

| Component |
|---|
| Tris(2-ethylhexyl) (Solvent) |
| Dimethyl dichlorosilane (Silica) |
| Cycloaliphatic hydrocarbon resin (polymer) |
| Azelate bis (2-ethylhexyl) (plasticizer) |
| Tetrakis (3-(3,5-di-tert-butyl-4-hydroxyphenyl) propionate de pentaerythritol) (Antioxidant) |

The gel of one embodiment of the present invention was prepared according to the procedure shown in Table 12.

TABLE 12

| Time | T° C. Ins | T° C. Out | Actions | Comments |
|---|---|---|---|---|
| 10 h | T° ambient | N/A | Introduction Solvent 117.71 g Heating start + Rotor | N/A |
| 10 h 30 | 133° C. | N/A | Add 41 g Plasticizer | Stop the rotor to add the Plasticizer |
| 11 H 05 | 135° C. | N/A | Add 89.30 g Cycloaliphatic hydrocarbon resin 5300 | N/A |
| 11 H 45 | 131° C. | N/A | Add 11 g Silica Rotor 150 RPM | N/A |
| 12 H 45 | 133° C. | N/A | Add 0.11 g antioxidant | N/A |
| 13 H 15 | 134° C. | N/A | Vaccum 20 mbar | Bubble removal |
| 14 H 15 | 133° C. | N/A | End of mixing and transfer to a glass jar | Homogeneous gel of light yellow colour |

The formulation provided a homogeneous thixotropic gel with light yellow colour.

The formulation of the thixotropic gel of the present invention prepared according to the method shown in Table 12 is shown in Table 13:

TABLE 13

| QTY Component | Tris(2-ethylhexyl) Solvent | Dimethyl dichlorosilane Silica | Cycloaliphatic hydrocarbon Resin Polymer | Azelate bis (2-ethylhexyl) plasticizer | Tetrakis (3-(3,5-di-tert-butyl-4-hydroxyphenyl) propionate de pentaerythritol) (Antioxidant) Antioxidant |
|---|---|---|---|---|---|
| 259.12 g 100% | 117.71 g 45.42% | 11 g 4.24% | 89.30 g 34.46% | 41 g 15.82% | 0.11 g 0.042% |

Example 9

A blood separation test was carried out to compare the convalescent plasma gel according to Example 8 ("Plasma convalescent gel 2") with comparative gels, the PS gel and the Regen-B gel, and with the convalescent plasma gel according to Table 7/Example 4 ("Plasma convalescent gel").

Each gel was filled into a 20 ml tube. The three tubes contain 6 g of gel and 2 ml of sodium citrate and 20 ml of vacuum. The tubes were then steam sterilized. Then three blood samples were taken, one per type from the same donor. Finally, the three tubes were placed in a centrifuge for 20 min. Each plasma obtained was tested without resuspension on the Syxmex XN-350 cell counter.

The results are shown in Table 14:

TABLE 14

| Recovery Results | | | | |
|---|---|---|---|---|
| Parameters | Plasma convalescent Gel | Regen-B | PS Gel | Plasma convalescent gel 2 |
| Platelets | 34/10^3 uL | 232/10^3 uL | 180/10^3 uL | 4/10^3 uL |
| Red blood cell | 0.40/10^3 uL | 0.02/10^3 uL | 0.01/10^3 uL | 0./10^3 uL |
| White blood Cell | 0/10^3 uL | 2.07/10^3 uL | 0.11/10^ uL | 0/10^3 uL |

The results indicate that both of the convalescent plasma gels (Example 8 & Example 4) remove more blood than the comparative gels (Regen-B and PS Gel). Furthermore, the results indicate that the convalescent plasma gel according to Example 8 ("Plasma convalescent gel 2") removes more blood cells than the convalescent plasma gel according to Table 7/Example 4 ("Plasma convalescent gel").

Definitions

The terms "treating", "treat" and "treatment" as used with respect to the methods described herein refer to eliminating, reducing, suppressing or ameliorating, either temporarily or permanently, either partially or completely, a clinical symptom, manifestation or progression of an event, disease or condition, such as, for example, coronavirus infections and conditions associated with such infections. Such treating need not be absolute to be useful.

The terms "effective amount", "therapeutically effective amount" and "amount effective to treat" as used herein refers to at least an amount effective, at dosages and for periods of time necessary, to achieve a desired therapeutic result, such as for example, a detectable (e.g., measureable), positive effect or improvement on any symptom, aspect, parameter or characteristics of a disease state or condition when administered to a subject. An effective amount can be provided in one or more administrations. Such effect amount need not be absolute to be beneficial.

Plasma is the largest component of blood, making up about 55 percent of its overall content, and when isolated, is a light yellow, straw-colored liquid. Along with water, salts and enzymes, plasma also contains immunoglobulins (antibodies), clotting factors, and the proteins albumin and fibrinogen. The components of the plasma are well known in the art (see e.g., Philip Westerman, Plasma Proteins, VIT1 to VIIT13, Sep. 17, 2002). Serum is also well defined and generally called as blood plasma without fibrinogen and other clotting factors. The source of plasma used in the composition of the present disclosure is preferably of the same mammalian species as the subject (e.g., human).

What is claimed is:

1. A container configured that is:

(i) prefilled with at the least a thixotropic gel characterized by a density selected from about 1.02 g/$cm^3$ to about 1.05 g/$cm^3$, wherein said container is prefilled only with said thixotropic gel as layer from the distal end of said container, or (ii) prefilled only with:

a) a thixotropic gel characterized by a density selected from about 1.02 g/$cm^3$ to about 1.05 g/$cm^3$, and b) an anticoagulant, wherein said thixotropic gel is the first layer from the distal end of said container, followed by a second layer consisting of said anticoagulant, and wherein said anticoagulant comprises sodium citrate, or (iii) prefilled only with:

a) a thixotropic gel characterized by a density selected from about 1.02 g/$cm^3$ to about 1.05 g/$cm^3$, and b) a coagulation activator, wherein said thixotropic gel is the first layer from the distal end of said container, followed by a second layer consisting of said coagulation activator, wherein said coagulation activator comprises calcium gluconate, wherein said thixotropic gel is selected among an oligomer, polymer, polyolefin hydrocarbon oligomer, an acrylic resin mixture, a PEG-Silica Gel or any combination thereof, and in which the thixotropic gel is selected from: a polyoxyalkylene polyol, trioctyl trimellitate, a hydrocarbonated resin, silica dimethyl silylate, or any combination thereof, and wherein the polyoxyalkylene polyol is selected from: polyethylene and/or polypropylene glycol trimethylolpropane ether, methyloxirane polymer with oxirane, ether with 2-ethyl-2-(hydroxymethyl)-1, 3-propanediol; poly (oxyethylene and/or oxypropylene) trimethylolpropane ether, trimethylol propane, ethoxylated trimethylolpropane, propxylated trimethylol propane, or any combination thereof.

2. The container according to claim 1, wherein said density is selected from about 1.04 g/$cm^3$ to about 1.045 g/$cm^3$.

3. A container configured to be that is:

(i) prefilled with at the least a thixotropic gel characterized by a density selected from about 1.02 g/$cm^3$ to about 1.05 g/$cm^3$, wherein said container is prefilled only with said thixotropic gel as layer from the distal end of said container, or (ii) prefilled only with:

a) a thixotropic gel characterized by a density selected from about 1.02 g/$cm^3$ to about 1.05 g/$cm^3$, and b) an anticoagulant, wherein said thixotropic gel is the first layer from the distal end of said container, followed by a second layer consisting of said anticoagulant, and wherein said anticoagulant comprises sodium citrate, or (iii) prefilled only with:

a) a thixotropic gel characterized by a density selected from about 1.02 g/$cm^3$ to about 1.05 g/$cm^3$, and b) a coagulation activator, wherein said thixotropic gel is the first layer from the distal end of said container, followed by a second layer consisting of said coagulation activator, wherein said coagulation activator comprises calcium gluconate, and wherein said thixotropic gel comprises trioctyl trimellitate, silica, hydrocarbon resin, polyol, phenol(s) and phosphite ester.

4. The container according to claim 3, wherein said trioctyl trimellitate is Tris (2 ethyhexyl), said silica is Dimethtyl dichlorosilane, said hydrocarbon resin is Cycloaliphatic hydrocarbon Resin, said polyol is Polyalkylene Polyol, said phenol(s) is Tetrakis (3-(3,5-di-tert-butyl-4-hydroxyphenyl) propionate of pentaerythritol) and said phosphite ester is Phosphite of tris (2,4-di-tert-butylphenyle).

5. The container as claimed in claim 3, wherein said thixotropic gel comprises trioctyl trimellitate in the range of 40-60%, silica in the range of 2-10%, hydrocarbon resin in the range of 30-60%, polyol in the range of 1-5%, phenol(s) in the range of 0-1%, and phosphite ester in the range of 0% to 0.06%.

6. The container according to claim 5, wherein said thixotropic gel comprises trioctyl trimellitate at about 50.96%, silica at about 4.21%, hydrocarbon resin at about 43%, polyol at about 1.73%, phenol(s) at about 0.05%, and phosphite ester at about 0.05%.

7. A container that is:

(i) prefilled with at the least a thixotropic gel characterized by a density selected from about 1.02 g/$cm^3$ to about 1.05 g/$cm^3$, wherein said container is prefilled only with said thixotropic gel as layer from the distal end of said container, or (ii) prefilled only with:

a) a thixotropic gel characterized by a density selected from about 1.02 g/$cm^3$ to about 1.05 g/$cm^3$, and b) an optional anticoagulant, wherein said thixotropic gel is the first layer from the distal end of said container, followed by a second layer consisting of said anticoagulant, and wherein said anticoagulant comprises sodium citrate, or (iii) prefilled only with:

a) a thixotropic gel characterized by a density selected from about 1.02 g/$cm^3$ to about 1.05 g/$cm^3$, and b) a coagulation activator, wherein said thixotropic gel is the first layer from the distal end of said container, followed by a second layer consisting of said coagulation activator, wherein said coagulation activator comprises calcium gluconate, and wherein said thixotropic gel comprises trioctyl trimellitate, silica, hydrocarbon resin, azelate ester and phosphite ester, wherein said trioctyl trimellitate is Tris (2 ethyhexyl), said silica is Dimethtyl dichlorosilane, said hydrocarbon resin is Cycloaliphatic hydrocarbon Resin, said azelate esters is Azelate de bis (2-ethylhexyle), and said phenol(s) is Tetrakis (3-(3, 5-di-tert-butyl-4-hydroxyphenyl) propionate of pentaerythritol).

8. The container according to claim 7, wherein said thixotropic gel comprises trioctyl trimellitate in the range of 35-55%, silica in the range of 2-10%, hydrocarbon resin in the range of 20-40%, azelate esters in the range of 10-30%, and phenol(s) in the range of 0-1%, wherein said thixotropic gel comprises trioctyl trimellitate at about 50.96%, silica at about 4.21%, hydrocarbon resin at about 43%, azelate esters at about 15.82%, and phenol(s) at about 0.05%.

* * * * *